(12) United States Patent
Su et al.

(10) Patent No.: US 11,508,102 B2
(45) Date of Patent: Nov. 22, 2022

(54) SYSTEMS AND METHODS FOR IMAGE PROCESSING

(71) Applicant: SHANGHAI UNITED IMAGING HEALTHCARE CO., LTD., Shanghai (CN)

(72) Inventors: Bin Su, Shanghai (CN); Yanyan Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 75 days.

(21) Appl. No.: 16/808,534

(22) Filed: Mar. 4, 2020

(65) Prior Publication Data
US 2020/0334871 A1 Oct. 22, 2020

(30) Foreign Application Priority Data

Apr. 19, 2019 (CN) .......................... 201910319178.5

(51) Int. Cl.
*G06K 9/00* (2022.01)
*G06T 11/00* (2006.01)
*A61B 5/055* (2006.01)
*A61B 5/00* (2006.01)
*A61B 6/03* (2006.01)
(Continued)

(52) U.S. Cl.
CPC ............ *G06T 11/008* (2013.01); *A61B 5/055* (2013.01); *A61B 5/7203* (2013.01); *A61B 5/7267* (2013.01); *A61B 6/032* (2013.01); *A61B 6/037* (2013.01); *A61B 6/5258* (2013.01); *A61B 8/5269* (2013.01); *G06T 5/003* (2013.01); *G06T 5/50* (2013.01); *G06T 7/0014* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20081* (2013.01); *G06T 2207/20084* (2013.01); *G06T 2207/30008* (2013.01); *G06T 2207/30016* (2013.01); *G06T 2207/30048* (2013.01); *G06T 2207/30092* (2013.01); *G06T 2207/30101* (2013.01)

(58) Field of Classification Search
CPC ...................................................... G06T 11/008
See application file for complete search history.

(56) References Cited

U.S. PATENT DOCUMENTS

2017/0039706 A1* 2/2017 Mikhno ................. A61B 6/481
2019/0059780 A1* 2/2019 Lee ....................... A61B 5/7207
(Continued)

*Primary Examiner* — Oneal R Mistry
(74) *Attorney, Agent, or Firm* — Metis IP LLC

(57) ABSTRACT

The present disclosure is related to systems and methods for image processing. The method may include obtaining an image including at least one of a first type of artifact or a second type of artifact. The method may include determining, based on a trained machine learning model, at least one of first information associated with the first type of artifact or second information associated with the second type of artifact in the image. The trained machine learning model may include a first trained model and a second trained model. The first trained model may be configured to determine the first information. The second trained model may be configured to determine the second information. The method may include generating a target image based on at least part of the first information and the second information.

15 Claims, 13 Drawing Sheets

(51) Int. Cl.
*A61B 6/00* (2006.01)
*A61B 8/08* (2006.01)
*G06T 5/00* (2006.01)
*G06T 5/50* (2006.01)
*G06T 7/00* (2017.01)

(56) References Cited

U.S. PATENT DOCUMENTS

2019/0287674 A1\* 9/2019 Nitta ................. G06V 10/454
2021/0177296 A1\* 6/2021 Saalbach ............. A61B 5/7267

\* cited by examiner

SYSTEMS AND METHODS FOR IMAGE PROCESSING

CROSS-REFERENCE TO RELATED APPLICATIONS

This application claims priority of Chinese Patent Application No. 201910319178.5, filed on Apr. 19, 2019, the contents of which are hereby incorporated by reference.

TECHNICAL FIELD

This disclosure generally relates to a system and method for image processing, and more particularly, relates to systems and methods for correcting an artifact in an image.

BACKGROUND

An image taken by an imaging system, such as a computed tomography (CT) system, may have different types of artifacts due to a variety of factors, such as a beam hardening. CT images are inherently more prone to artifacts than conventional radiographs because the image is reconstructed from signals from numerous (on an order of a million) independent detector measurements. The reconstruction technique assumes that all these measurements are consistent, so any error of measurement may usually reflect itself as an error in the reconstructed image. For example, bone induced artifacts caused by spectral absorption of the skull of a patient are commonly observed in a head CT image. Artifacts usually blur an image and further affect a diagnostic power of CT. Several algorithms have been proposed to address the artifacts, but most are complex and take a long processing time. Therefore, it is desirable to provide systems and methods for correcting an artifact in an image effectively.

SUMMARY

According to an aspect of the present disclosure, a system may include at least one storage device storing a set of instructions, and at least one processor in communication with the at least one storage device. When executing the stored set of instructions, the at least one processor may cause the system to perform a method. The method may include obtaining an image including at least one of a first type of artifact or a second type of artifact. The method may include determining, based on a trained machine learning model, at least one of first information associated with the first type of artifact or second information associated with the second type of artifact in the image. The trained machine learning model may include a first trained model and a second trained model. The first trained model may be configured to determine the first information. The second trained model may be configured to determine the second information. The method may include generating a target image based on at least part of the first information and the second information.

In some embodiments, the trained machine learning model may be obtained according to a process. The process may include obtaining a plurality of training samples. The plurality of training samples may include a plurality of sample input images and a plurality of corresponding sample expected images. Each of the plurality of corresponding sample expected images may be determined by performing an artifact correction operation on a sample input image. The process may include determining the trained machine learning model by training, based on the plurality of training samples, a preliminary machine learning model.

In some embodiments, the preliminary machine learning model may include a first preliminary model and a second preliminary model. The process may include determining the first trained model by inputting the plurality of sample input images and a plurality of first residual images into the first preliminary model. Each of the plurality of first residual images may relate to a difference between a sample input image and a corresponding sample expected image.

In some embodiments, the first trained model or the second trained model may include at least one of a U-shape network (UNet), a residual network (ResNet), a dense convolutional network (DenseNet), or a generative adversarial network (GAN).

In some embodiments, the process may include determining the difference between a sample input image and a corresponding sample expected image by performing a subtraction operation between the sample input image and the corresponding sample expected image.

In some embodiments, the process may include determining a plurality of sample intermediate images by inputting the plurality of sample input images into the first trained model. The process may include determining the second trained model by inputting the plurality of sample intermediate images and a plurality of second residual images into the second preliminary model. Each of the plurality of second residual images may relate to a difference between a sample intermediate image and a corresponding first residual image.

In some embodiments, the process may include determining the difference between a sample intermediate image and a corresponding first residual image by performing a subtraction operation between the sample intermediate image and the corresponding first residual image.

In some embodiments, the method may include determining a second image by performing a down-sampling operation on the image. The method may include determining, based on the trained machine learning model, at least one of third information associated with the first type of artifact or fourth information associated with the second type of artifact in the second image. The method may include determining the at least one of the first information or the second information by performing an up-sampling operation on the at least one of the third information or the fourth information.

In some embodiments, the up-sampling operation may include a linear interpolation operation.

In some embodiments, the first type of artifact may include a low frequency artifact, and the second type of artifact may include a high frequency artifact.

In some embodiments, at least one of the first type of artifact or the second type of artifact may be a bone induced artifact.

In some embodiments, the trained machine learning model may be a convolutional neural network (CNN).

In some embodiments, the image may include at least one of a computed tomography (CT) image, a magnetic resonance imaging (MRI) image, a positron emission tomography (PET) image, an ultrasound image, or an X-ray image.

According to an aspect of the present disclosure, a system may include at least one storage device storing a set of instructions, and at least one processor in communication with the at least one storage device. When executing the stored set of instructions, the at least one processor may cause the system to perform a method. The method may include obtaining an image including at least one of a first type of artifact or a second type of artifact. The method may include generating a target image by processing, based on a trained machine learning mode, the image. The trained machine learning mode may include a first trained model and a second trained model. The first trained model may be configured to correct the first type of artifact in the image. The second trained model may be configured to correct the second type of artifact in the image.

In some embodiments, the trained machine learning model may be obtained according to a process. The process may include obtaining a plurality of training samples. The plurality of training samples may include a plurality of sample input images and a plurality of corresponding sample expected images. Each of the plurality of corresponding sample expected images may be determined by performing an artifact correction operation on a sample input image. The process may include determining the trained machine learning model by training, based on the plurality of training samples, a preliminary machine learning model.

In some embodiments, the process may include determining the first trained model by inputting the plurality of sample input images and the plurality of corresponding sample expected images into the first preliminary model.

In some embodiments, the process may include determining a plurality of sample intermediate images by inputting the plurality of sample input images into the first trained model. The process may include determining the second trained model by inputting the plurality of sample intermediate images and the plurality of corresponding sample expected images into the second preliminary model.

In some embodiments, the first type of artifact may include a low frequency artifact. The second type of artifact may include a high frequency artifact.

In some embodiments, at least one of the first type of artifact or the second type of artifact may be a bone induced artifact.

In some embodiments, the trained machine learning model may be a convolutional neural network (CNN).

In some embodiments, the first trained model or the second trained model may include at least one of a U-shape network (UNet), a residual network (ResNet), a dense convolutional network (DenseNet), or a generative adversarial network (GAN).

In some embodiments, the image may include at least one of a computed tomography (CT) image, a magnetic resonance imaging (MRI) image, a positron emission tomography (PET) image, an ultrasound image, or an X-ray image.

According to another aspect of the present disclosure, a method for image processing may be implemented on a computing device having one or more processors and one or more storage devices. The method may include obtaining an image including at least one of a first type of artifact or a second type of artifact. The method may include determining, based on a trained machine learning model, at least one of first information associated with the first type of artifact or second information associated with the second type of artifact in the image. The trained machine learning model may include a first trained model and a second trained model. The first trained model may be configured to determine the first information. The second trained model may be configured to determine the second information. The method may include generating a target image based on at least part of the first information and the second information.

In some embodiments, the trained machine learning model may be obtained according to a process. The process may include obtaining a plurality of training samples. The plurality of training samples may include a plurality of sample input images and a plurality of corresponding sample expected images. Each of the plurality of corresponding sample expected images may be determined by performing an artifact correction operation on a sample input image. The process may include determining the trained machine learning model by training, based on the plurality of training samples, a preliminary machine learning model.

In some embodiments, the preliminary machine learning model may include a first preliminary model and a second preliminary model. The process may include determining the first trained model by inputting the plurality of sample input images and a plurality of first residual images into the first preliminary model. Each of the plurality of first residual images may relate to a difference between a sample input image and a corresponding sample expected image.

In some embodiments, the first trained model or the second trained model may include at least one of a U-shape network (UNet), a residual network (ResNet), a dense convolutional network (DenseNet), or a generative adversarial network (GAN).

In some embodiments, the process may include determining the difference between a sample input image and a corresponding sample expected image by performing a subtraction operation between the sample input image and the corresponding sample expected image.

In some embodiments, the process may include determining a plurality of sample intermediate images by inputting the plurality of sample input images into the first trained model. The process may include determining the second trained model by inputting the plurality of sample intermediate images and a plurality of second residual images into the second preliminary model. Each of the plurality of second residual images may relate to a difference between a sample intermediate image and a corresponding first residual image.

In some embodiments, the process may include determining the difference between a sample intermediate image and a corresponding first residual image by performing a subtraction operation between the sample intermediate image and the corresponding first residual image.

In some embodiments, the method may include determining a second image by performing a down-sampling operation on the image. The method may include determining, based on the trained machine learning model, at least one of third information associated with the first type of artifact or fourth information associated with the second type of artifact in the second image. The method may include determining the at least one of the first information or the second information by performing an up-sampling operation on the at least one of the third information or the fourth information.

In some embodiments, the up-sampling operation may include a linear interpolation operation.

In some embodiments, the first type of artifact may include a low frequency artifact, and the second type of artifact may include a high frequency artifact.

In some embodiments, at least one of the first type of artifact or the second type of artifact may be a bone induced artifact.

In some embodiments, the trained machine learning model may be a convolutional neural network (CNN).

In some embodiments, the image may include at least one of a computed tomography (CT) image, a magnetic resonance imaging (MRI) image, a positron emission tomography (PET) image, an ultrasound image, or an X-ray image.

According to another aspect of the present disclosure, a method for image processing may be implemented on a computing device having one or more processors and one or more storage devices. The method may include obtaining an image including at least one of a first type of artifact or a second type of artifact. The method may include generating a target image by processing, based on a trained machine learning mode, the image. The trained machine learning mode may include a first trained model and a second trained model. The first trained model may be configured to correct the first type of artifact in the image. The second trained model may be configured to correct the second type of artifact in the image.

In some embodiments, the trained machine learning model may be obtained according to a process. The process may include obtaining a plurality of training samples. The plurality of training samples may include a plurality of sample input images and a plurality of corresponding sample expected images. Each of the plurality of corresponding sample expected images may be determined by performing an artifact correction operation on a sample input image. The process may include determining the trained machine learning model by training, based on the plurality of training samples, a preliminary machine learning model.

In some embodiments, the process may include determining the first trained model by inputting the plurality of sample input images and the plurality of corresponding sample expected images into the first preliminary model.

In some embodiments, the process may include determining a plurality of sample intermediate images by inputting the plurality of sample input images into the first trained model. The process may include determining the second trained model by inputting the plurality of sample intermediate images and the plurality of corresponding sample expected images into the second preliminary model.

In some embodiments, the first type of artifact may include a low frequency artifact. The second type of artifact may include a high frequency artifact.

In some embodiments, at least one of the first type of artifact or the second type of artifact may be a bone induced artifact.

In some embodiments, the trained machine learning model may be a convolutional neural network (CNN).

In some embodiments, the first trained model or the second trained model may include at least one of a U-shape network (UNet), a residual network (ResNet), a dense convolutional network (DenseNet), or a generative adversarial network (GAN).

In some embodiments, the image may include at least one of a computed tomography (CT) image, a magnetic resonance imaging (MRI) image, a positron emission tomography (PET) image, an ultrasound image, or an X-ray image.

According to still another aspect of the present disclosure, a non-transitory computer readable medium may include at least one set of instructions. When executed by at least one processor of a computing device, the at least one set of instructions may cause the at least one processor to effectuate a method. The method may include obtaining an image including at least one of a first type of artifact or a second type of artifact. The method may include determining, based on a trained machine learning model, at least one of first information associated with the first type of artifact or second information associated with the second type of artifact in the image. The trained machine learning model may include a first trained model and a second trained model. The first trained model may be configured to determine the first information. The second trained model may be configured to determine the second information. The method may include generating a target image based on at least part of the first information and the second information.

According to still another aspect of the present disclosure, a non-transitory computer readable medium may include at least one set of instructions. When executed by at least one processor of a computing device, the at least one set of instructions may cause the at least one processor to effectuate a method. The method may include obtaining an image including at least one of a first type of artifact or a second type of artifact. The method may include generating a target image by processing, based on a trained machine learning mode, the image. The trained machine learning mode may include a first trained model and a second trained model. The first trained model may be configured to correct the first type of artifact in the image. The second trained model may be configured to correct the second type of artifact in the image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
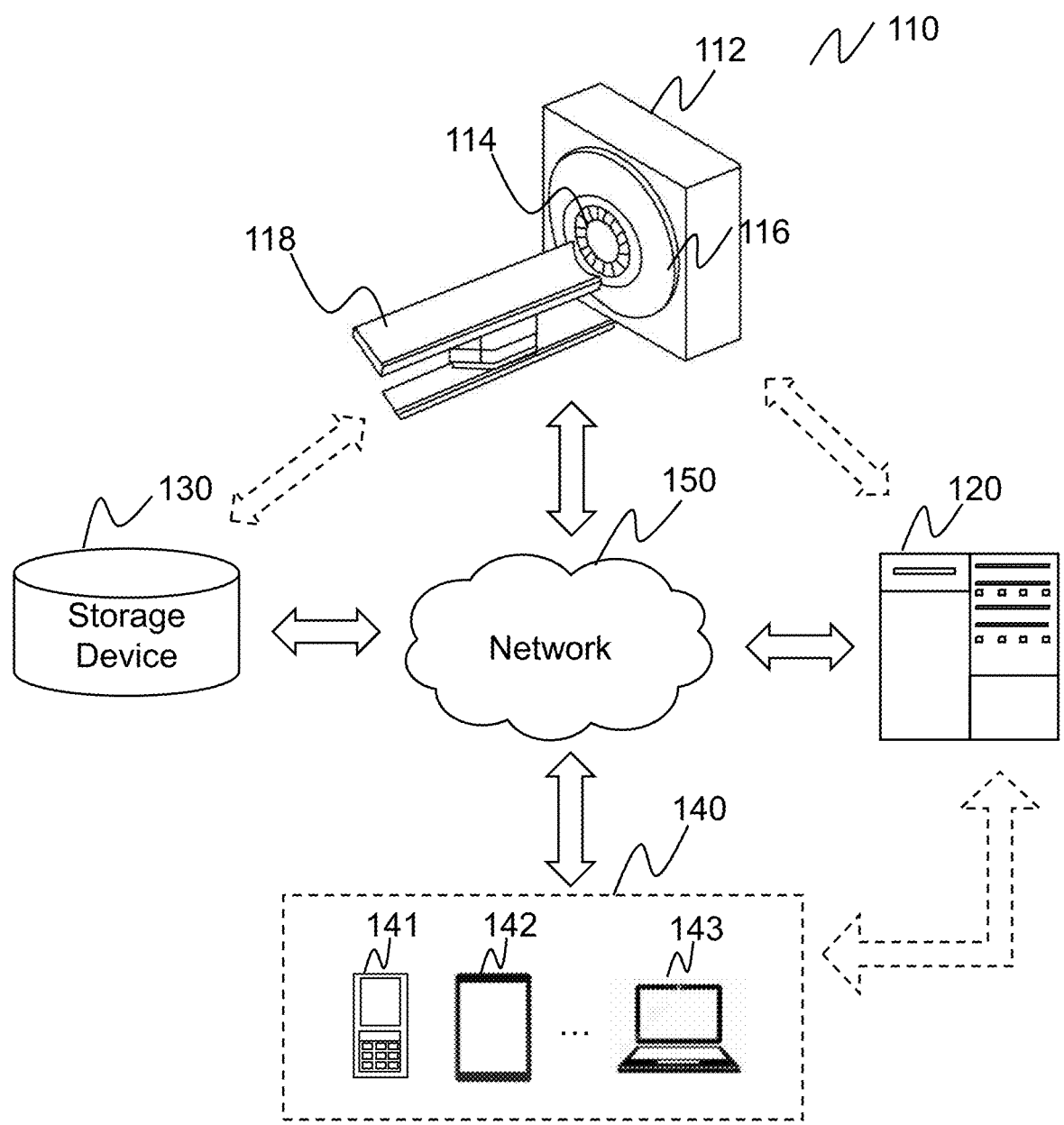
FIG. 1 is a schematic diagram illustrating an exemplary image processing system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements.

In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an artifact correction process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

In computed tomography (CT), a beam hardening artifact may be one kind of common artifact in a CT image. For example, bone induced artifacts that stem from the energy-dependent attenuation of skull may be commonly observed in head CT images. Various correction techniques have been proposed to address the beam hardening artifact. Existing correction techniques may be classified into hardware correction techniques and software correction techniques. In the hardware correction techniques, a correction tool (e.g., a metal plate, a water bag) may be used to correct the beam hardening artifact. Exemplary hardware correction techniques may include a water bag correction technique, a prefiltration correction technique, or the like. In the prefiltration correction technique, one or more filters (e.g., one or more thin metal plates) may be placed between an X-ray source and a subject to be scanned to narrow a broad source spectrum. The prefiltration correction technique may be easy to implement, but a signal to noise ratio of scanned data may decrease, as the filters absorb parts of the X-ray photons. In the water bag correction technique, a subject to be scanned may be surrounded by a water bag. Putting the subject inside a cylindrical container filled with a liquid material that has the same or similar X-ray attenuation properties may ensure that rays from all directions undergo nearly a same beam hardening effect. However, the use of the water bag may be inconvenient.

The software correction techniques may be to eliminate the artifacts by processing image data before and/or after an image reconstruction process. Exemplary software correction techniques may include a fitting technique (e.g., a polynomial fitting, a monte carlo fitting), a linearization technique, an iterative technique, or the like. In the fitting technique, a correction phantom may be required. The material of the correction phantom may be the same as the material of a subject to be scanned. Since a human is composed of complex elements, it is difficult to make the correction phantom, which may limit the use of the fitting technique in the artifact correction. The iterative technique may incorporate a polychromatism of an X-ray spectrum and a dependence of a attenuation with an X-ray energy into a image reconstruction model. In a dual energy technique, a energy-dependency of attenuation coefficients may be modeled as a linear combination of two basis functions representing separate contributions of a photo-electric effect and a scattering. The coefficients of the two basis functions may be needed for each image pixel. Therefore, two scans at different source voltages may be required, preferably with non-overlapping spectra. After the coefficients are determined, reconstructions of the linear attenuation coefficient may be estimated at any energy within the diagnostic range. However, most of these correction techniques are complex and take a long processing time.

An aspect of the present disclosure relates to a system and method for image processing. An image including at least one of a first type of artifact (e.g., a low frequency artifact) or a second type of artifact (e.g., a high frequency artifact) may be obtained. As used herein, an artifact may refer to any feature in an image which is not present in an original imaged subject. At least one of first information associated with the first type of artifact or second information associated with the second type of artifact in the image may be determined based on a trained machine learning model. In some embodiments, the trained machine learning model may be a two-step convolutional neural network (CNN). For example, the trained machine learning model may include a first trained model configured to determine the first information and a second trained model configured to determine the second information. A target image may be generated based on at least part of the first information and the second information. Therefore, artifacts in the image may be corrected based on the trained machine learning model without using X-ray spectrum information and detector information. With the assistance of deep learning, the artifact correction process may be simplified, and accordingly the efficiency of the correction process may be improved. Furthermore, different types of artifacts (e.g., the first type of artifact and the second type of artifact) in the image may be corrected using different network structures, which may improve the accuracy of the correction process.

FIG. 1 is a schematic diagram illustrating an exemplary image processing system according to some embodiments of the present disclosure. As shown, the image processing system 100 may include an imaging device 110, a processing device 120, a storage device 130, one or more terminal(s) 140, and a network 150. In some embodiments, the imaging device 110, the processing device 120, the storage device 130, and/or the terminal(s) 140 may be connected to and/or communicate with each other via a wireless connection (e.g., the network 150), a wired connection, or a combination thereof. The image processing system 100 may include various types of connection between its components. For example, the imaging device 110 may be connected to the processing device 120 through the network 150, or connected to the processing device 120 directly as illustrated by the bidirectional dotted arrow connecting the imaging device 110 and the processing device 120 in FIG. 1. As another example, the storage device 130 may be connected to the processing device 120 through the network 150, as illustrated in FIG. 1, or connected to the processing device 120 directly. As still another example, the terminal(s) 140 may be connected to the processing device 120 through the network 150, or connected to the processing device 120 directly as illustrated by the bidirectional dotted arrow connecting the terminal(s) 140 and the processing device 120 in FIG. 1. As still another example, the terminal(s) 140 may be connected to the imaging device 110 through the network 150, as illustrated in FIG. 1, or connected to the imaging device 110 directly. As still another example, the storage device 130 may be connected to the imaging device 110 through the network 150, or connected to the imaging device 110 directly as illustrated by the bidirectional dotted arrow connecting the imaging device 110 and the storage device 130 in FIG. 1.

The imaging device 110 may be configured to image a subject using radiation rays and generate imaging data used to generate one or more images relating to the subject. In some embodiments, the imaging device 110 may transmit the imaging data to the processing device 120 or the terminal 140 for further processing (e.g., generating one or more images). In some embodiments, the imaging data and/or the one or more images associated with the subject may be stored in the storage device 130, the processing device 120, and/or the terminal 140.

In some embodiments, the imaging device 110 may be a computed tomography (CT) device, a magnetic resonance imaging (MRI) device, a positron emission tomography (PET) device, an ultrasound device, an X-ray imaging device, a digital subtraction angiography (DSA) device, a dynamic spatial reconstruction (DSR) device, a multimodality device, or the like, or any combination thereof. Exemplary X-ray imaging devices may include a suspended X-ray imaging device, a digital radiography (DR) device (e.g., a mobile digital X-ray imaging device), a C-arm device, or the like. Exemplary CT devices may include a cone beam breast computed tomography (CBCT), or the like. Exemplary multimodality devices may include a computed tomography-positron emission tomography (CT-PET) device, a computed tomography-magnetic resonance imaging (CT-MRI) device, or the like. The subject may be biological or non-biological. In some embodiments, the subject may include a patient, a man-made object, etc. In some embodiments, the subject may include a specific portion, an organ, and/or tissue of a patient. For example, the subject may include head, brain, neck, body, shoulder, arm, thorax, cardiac, stomach, blood vessel, soft tissue, knee, feet, or the like, or any combination thereof.

In some embodiments, the imaging device 110 may include a gantry 112, a detector 114, a radiation source 116, and a table 118. The subject may be placed on the table 118 for imaging. In some embodiments, the radiation source 116 may include a high voltage generator (not shown in FIG. 1), a tube (not shown in FIG. 1) and a collimator (not shown in FIG. 1). The high voltage generator may be configured to generate a high-voltage and current for the tube. The tube may generate and/or emit radiation beams traveling toward the subject. The radiation beam may include a particle beam, a photon beam, or the like, or any combination thereof. The particle beam may include a stream of neutrons, protons, electrons, heavy ions, or the like, or any combination thereof. The photon beam may include an X-ray beam, a γ-ray beam, an α-ray beam, a β-ray beam, an ultraviolet beam, a laser beam, or the like, or any combination thereof. In some embodiments, the tube may include an anode target and a filament. The filament may be configured to generate electrons to bombard the anode target. The anode target may be configured to generate the radiation rays (e.g., X-rays) when the electrons bombard the anode target. The collimator may be configured to adjust the irradiation region (i.e., radiation field) on the subject.

The detector 114 may detect radiation beams. In some embodiments, the detector 114 may be configured to produce an analog electrical signal that represents the intensity of the received X-rays, including the attenuated beam, as it passes through the subject. In some embodiments, the detector 114 may be a flat panel detector. In some embodiments, the detector 114 may include a plurality of detecting units. The detecting units may include a scintillation detector (e.g., a cesium iodide detector), a gas detector, etc. The plurality of detecting units of the detector may be arranged in any suitable manner, for example, a single row, two rows, or another number of rows.

The processing device 120 may process data and/or information obtained from the imaging device 110, the storage device 130, and/or the terminal(s) 140. For example, the processing device 120 may obtain an image including at least one of a first type of artifact or a second type of artifact. As another example, the processing device 120 may determine, based on a trained machine learning model, at least one of first information associated with a first type of artifact or second information associated with a second type of artifact in an image. As a further example, the processing device 120 may generate a target image based on at least part of first information and second information. As a further example, the processing device 120 may determine a trained machine learning model by training a preliminary machine learning model. As a still further example, the processing device 120 may generate a target image by processing, based on a trained machine learning mode, an image. In some embodiments, the processing device 120 may be a single server or a server group. The server group may be centralized or distributed. In some embodiments, the processing device 120 may be local or remote. For example, the processing device 120 may access information and/or data from the imaging device 110, the storage device 130, and/or the terminal(s) 140 via the network 150. As another example, the processing device 120 may be directly connected to the imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the imaging device 110.

The storage device 130 may store data, instructions, and/or any other information. In some embodiments, the storage device 130 may store data obtained from the imaging device 110, the processing device 120, and/or the terminal(s) 140. For example, the storage device 130 may store an image including at least one of a first type of artifact or a second type of artifact obtained from an imaging device (e.g., the imaging device 110). As another example, the storage device 130 may store first information associated with a first type of artifact and second information associated with a second type of artifact in an image determined by the processing device 120. As still another example, the storage device 130 may store a trained machine learning model. As a further example, the storage device 130 may store a target image generated by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the image processing system 100 (e.g., the processing device 120, the terminal(s) 140). One or more components in the image processing system 100 may access the data or instructions stored in the storage device 130 via the network 150. In some embodiments, the storage device 130 may be integrated into the imaging device 110.

The terminal(s) 140 may be connected to and/or communicate with the imaging device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the image processing system 100. In some embodiments, one or more components of the image processing system 100 (e.g., the imaging device 110, the processing device 120, the storage device 130, the terminal(s) 140, etc.) may communicate information and/or data with one or more other components of the image processing system 100 via the network 150. For example, the processing device 120 and/or the terminal 140 may obtain an image from the imaging device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the image processing system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the storage device 130 may be data storage including cloud computing platforms, such as a public cloud, a private cloud, community, and hybrid clouds, or the like.

Figure 2:
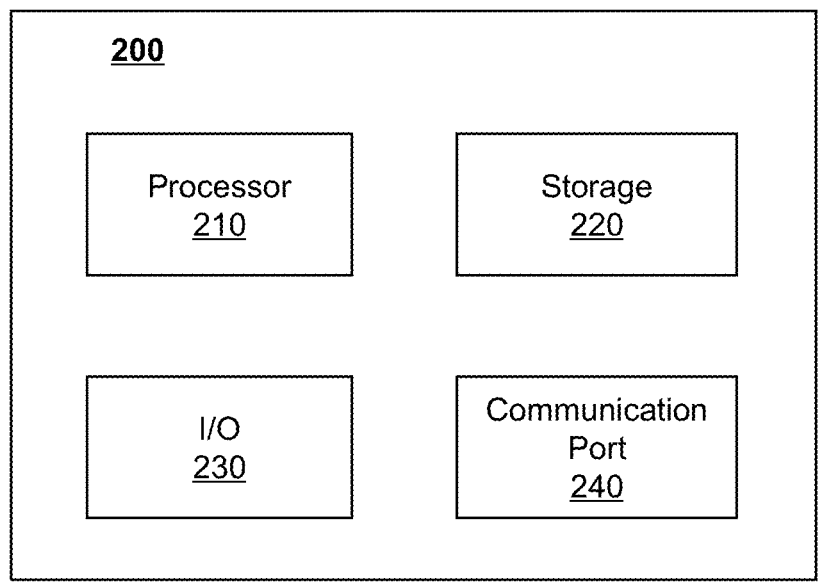
FIG. 2 is a schematic diagram illustrating exemplary hardware and/or software components of an exemplary computing device on which the processing device may be implemented according to some embodiments of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process imaging data obtained from the imaging device 110, the terminal(s) 140, the storage device 130, and/or any other component of the image processing system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal(s) 140, the storage device 130, and/or any other component of the image processing system 100. The storage 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the imaging device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
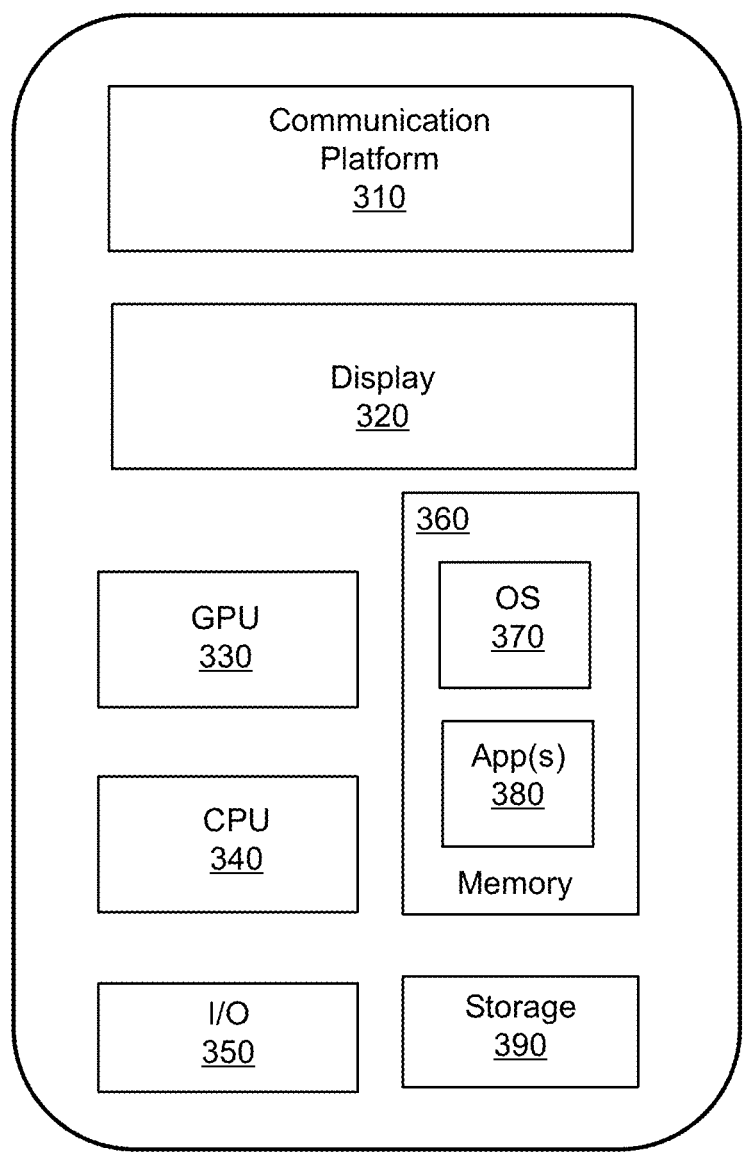
FIG. 3 is a schematic diagram illustrating exemplary hardware and/or software components of an exemplary mobile device on which the terminal(s) may be implemented according to some embodiments of the present disclosure.

FIG. 3 is a schematic diagram illustrating exemplary hardware and/or software components of an exemplary mobile device 300 on which the terminal(s) 140 may be implemented according to some embodiments of the present disclosure.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the image processing system 100, and enable data and/or signal to be transmitted between the mobile device 300 and other components of the image processing system 100. For example, the communication platform 310 may establish a wireless connection between the mobile device 300 and the imaging device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the image processing system 100. For example, the communication platform 310 may transmit data and/or signals inputted by a user to other components of the image processing system 100. The inputted data and/or signals may include a user instruction. As another example, the communication platform 310 may receive data and/or signals transmitted from the processing device 120. The received data and/or signals may include imaging data acquired by a detector of the imaging device 110.

In some embodiments, a mobile operating system (OS) 370 (e.g., iOS™ Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information respect to an image processing operation or other information from the processing device 120. User interactions with the information stream may be achieved via the I/O 350 and provided to the processing device 120 and/or other components of the image processing system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
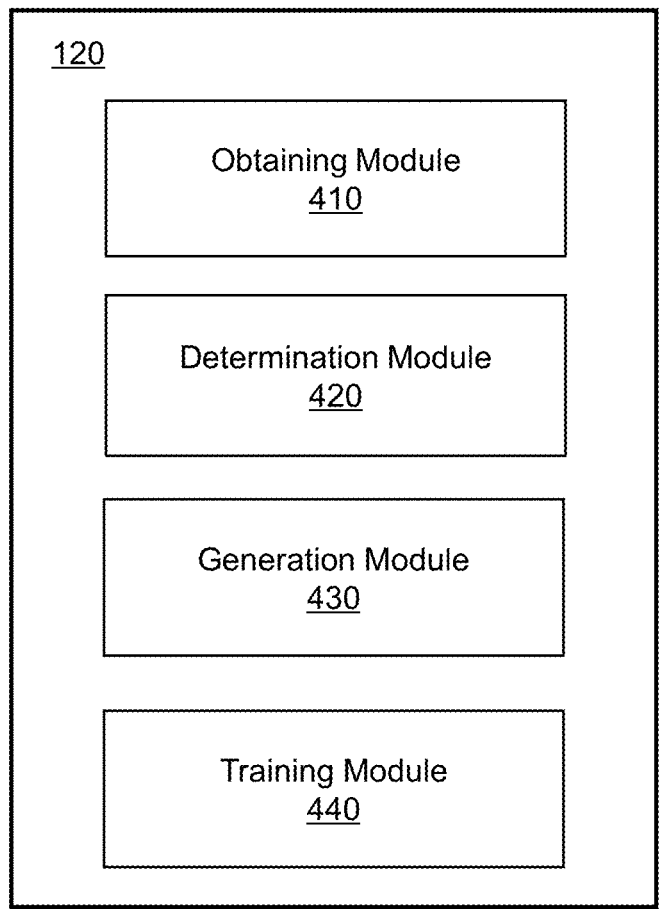
FIG. 4 is a schematic diagram illustrating an exemplary processing device according to some embodiments of the present disclosure.

FIG. 4 is a schematic diagram illustrating an exemplary processing device according to some embodiments of the present disclosure. In some embodiments, the processing device 120 may include an obtaining module 410, a determination module 420, a generation module 430, and a training module 440. The modules may be hardware circuits of at least part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application or set of instructions.

The obtaining module 410 may be configured to obtain data and/or information associated with the image processing system 100. The data and/or information associated with the image processing system 100 may include an image, first information associated with a first type of artifact, second information associated with a second type of artifact, a preliminary machine learning model, a trained machine learning model, a plurality of training samples, or the like, or any combination thereof. For example, the obtaining module 410 may obtain an image to be processed. The image may include a first type of artifact (e.g., a low frequency artifact) and/or a second type of artifact (e.g., a high frequency artifact). As another example, the obtaining module 410 may obtain a plurality of training samples. The plurality of training samples may include a plurality of sample input images and a plurality of corresponding sample expected images. In some embodiments, the obtaining module 410 may obtain the data and/or information associated with the image processing system 100 from one or more components (e.g., the imaging device 110, the storage device 130, the terminal 140 of the image processing system 100 or an external storage device via the network 150.

The determination module 420 may be configured to determine data and/or information associated with the image processing system 100. In some embodiments, the determination module 420 may determine first information associated with a first type of artifact and/or second information associated with a second type of artifact in an image based on a trained machine learning model. For example, the determination module 420 may determine a second image by performing a down-sampling operation on an image. The determination module 420 may determine third information associated with a first type of artifact and fourth information associated with a second type of artifact in the second image based on a trained machine learning model. The determination module 420 may determine first information and second information in the image by performing an up-sampling operation on the third information and the fourth information in the second image. More descriptions of the determination of the first information and the second information may be found elsewhere in the present disclosure (e.g., FIGS. 5, 6, and descriptions thereof).

The generation module 430 may be configured to generate a target image (e.g., a corrected image). For example, the generation module 430 may generate a target image based on at least part of the first information and the second information. As another example, the generation module 430 may generate a target image by processing an image based on a trained machine learning model. More descriptions of the generation of the target image may be found elsewhere in the present disclosure (e.g., FIGS. 5, 8, and descriptions thereof).

The training module 440 may be configured to determine a trained machine learning model. For example, the training module 440 may determine a first trained model by inputting a plurality of sample input images and a plurality of first residual images into a first preliminary model. The training module 440 may determine a plurality of sample intermediate images by inputting the plurality of sample input images into the first trained model. The training module 440 may determine a second trained model by inputting the plurality of sample intermediate images and a plurality of second residual images into a second preliminary model. As another example, the training module 440 may determine a first trained model by inputting a plurality of sample input images and a plurality of corresponding sample expected images into a first preliminary model. The training module 440 may determine a second trained model by inputting a plurality of sample intermediate images and the plurality of corresponding sample expected images into a second preliminary model. More descriptions of the determination of the trained machine learning model may be found elsewhere in the present disclosure (e.g., FIGS. 7, 9, and descriptions thereof).

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the determination module 420 and the generation module 430 may be combined into a single module, which may both determine first information associated with a first type of artifact and second information associated with a second type of artifact in an image and generate a target image. In some embodiments, one or more modules may be added or omitted in the processing device 120. For example, the processing device 120 may further include a storage module (not shown in FIG. 4) configured to store data and/or information (e.g., first information, second information, third information, fourth information) associated with an image. As another example, the determination module 420 may be omitted. As still another example, the training module 440 may be unnecessary and the trained machine learning model may be obtained from a storage device (e.g., the storage device 130).

Figure 5:
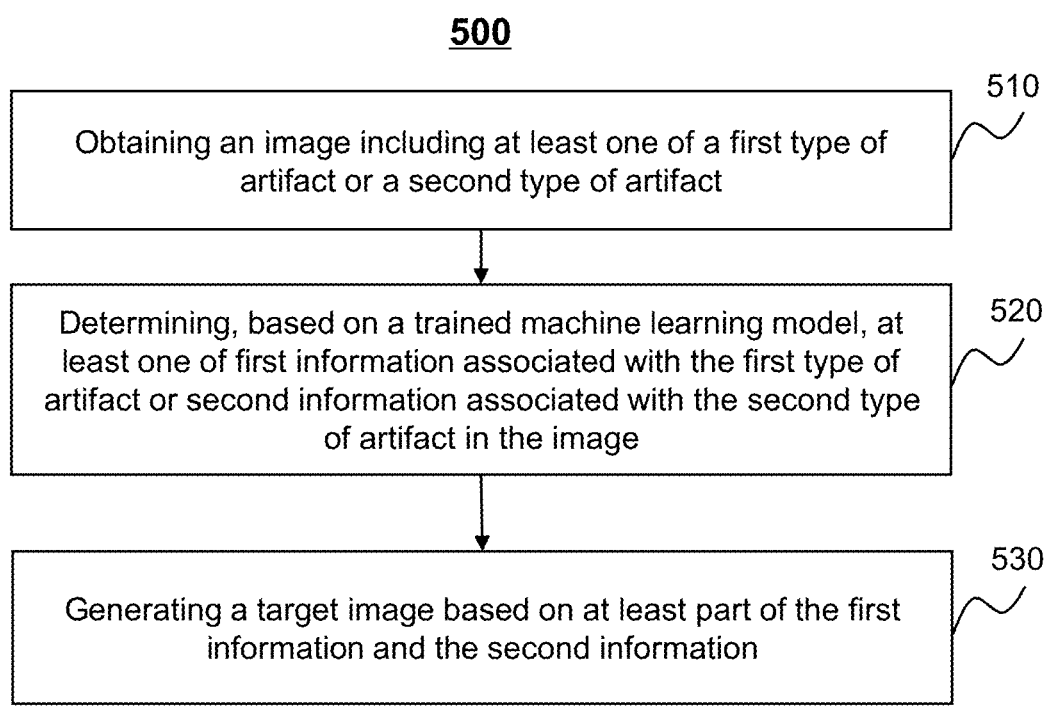
FIG. 5 is a flowchart illustrating an exemplary process for generating a target image according to some embodiments of the present disclosure.

FIG. 5 is a flowchart illustrating an exemplary process for generating a target image according to some embodiments of the present disclosure. In some embodiments, the process 500 may be implemented in the image processing system 100 illustrated in FIG. 1. For example, the process 500 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) may obtain an image including at least one of a first type of artifact or a second type of artifact.

In some embodiments, the processing device 120 may obtain the image from one or more components (e.g., the imaging device 110, the terminal 140, and/or the storage device 130) of the image processing system 100 or an external storage device via the network 150. In some embodiments, the processing device 120 may obtain the image from the I/O 230 of the computing device 200 via the communication port 240, and/or the I/O 350 of the mobile device 300 via the communication platform 310.

In some embodiments, the image may be a medical image. For example, the image may be associated with a specific portion (e.g., the head, the thorax, the abdomen), an organ (e.g., a lung, the liver, the heart, the stomach), and/or tissue (e.g., muscle tissue, connective tissue, epithelial tissue, nervous tissue) of a human or an animal. In some embodiments, the image may be an industrial image. For example, the image may be associated with a workpiece (e.g., an injection molded, cast, forged or fabricated workpiece made from metal, plastic, polymers, or composites).

In some embodiments, the image may include a CT image, an MRI image, a PET-CT image, an SPECT-MRI image, or the like. In some embodiments, the image may include a two-dimensional (2D) image, a three-dimensional (3D) image, a four-dimensional (4D) image, or the like. In some embodiments, the imaging device 110 may obtain projection data via imaging a subject or a part of the subject. The processing device 120 may generate the image based on projection data generated by the imaging device 110.

In some embodiments, the image may include at least one of the first type of artifact or the second type of artifact. As used herein, an artifact may refer to any feature in an image which is not present in an original imaged subject. In computed tomography (CT), an artifact may indicate a systematic discrepancy between CT numbers in a reconstructed image and true attenuation coefficients of a subject. In some embodiments, the first type of artifact may be a low frequency artifact, and the second type of artifact may be a high frequency artifact. As used herein, a low frequency in an image may refer to pixel values that are changing slowly over space, i.e. a low spatial frequency; a high frequency may refer to pixel values that are changing rapidly in space, i.e. a high spatial frequency. As used herein, a low frequency artifact may refer to an artiface of a low spatial frequency; a high frequency artifact may refer to an artiface of a high spatial frequency.

In some embodiments, the first type of artifact and/or the second type of artifact may include a cupping artifact, a streak artifact, a metal artifact, a high-density foreign material artifact, or the like, or any combination thereof. For example, the first type of artifact may be a cupping artifact and the second type of artifact may be a streak artifact. In some embodiments, the first type of artifact and/or the second type of artifact may be a bone induced artifact. For example, the first type of artifact and/or the second type of artifact may be a bone hardening artifact.

In 520, the processing device 120 (e.g., the determination module 420) may determine, based on a trained machine learning model, at least one of first information associated with the first type of artifact or second information associated with the second type of artifact in the image.

In some embodiments, the first information may be a first image associated with the first type of artifact, and the second information may be a second image associated with the second type of artifact. In some embodiments, the processing device 120 may determine the first information and the second information based on the image according to the trained machine learning model. In some embodiments, the trained machine learning model may be a two-step convolutional neural network (CNN). For example, the trained machine learning model may include a first trained model and a second trained model. The first trained model and the second trained model may be cascaded. That is, an output of the first trained model may be an input of the second trained model. The first trained model may be configured to determine the first information, and the second trained model may be configured to determine the second information. In some embodiments, the first trained model and/or the second trained model may include a U-shape network (UNet), a residual network (ResNet), a dense convolutional network (DenseNet), a generative adversarial network (GAN), or the like, or any combination thereof. For example, the first trained model may be a UNet, and the second trained model may be a ResNet.

The trained machine learning model may be determined by training a preliminary machine learning model. The preliminary machine learning model may include a first preliminary model and a second preliminary model. For example, the first trained model may be determined by training the first preliminary model, and the second trained model may be determined by training the second preliminary model. In some embodiments, the preliminary machine learning model (e.g., the first preliminary model, the second preliminary model) may include one or more algorithms used for generating an output result (e.g., the first information, the second information) based on input image data (e.g., the image). The trained machine learning model may include one or more relatively optimized parameters relating to the algorithms (e.g., the CNN) of the preliminary machine learning model, so that the sufficiency and/or accuracy of artifact removal based on the trained machine learning model may be satisfactory for practical use.

In some embodiments, the trained machine learning model may be generated by one or more other processors inside and/or outside the image processing system 100. In some embodiments, the processing device 120 may directly obtain the trained machine learning model, e.g., from the storage device 130. More descriptions of the determination of the trained machine learning model may be found elsewhere in the present disclosure (e.g., FIG. 7 and descriptions thereof).

In 530, the processing device 120 (e.g., the generation module 430) may generate a target image based on at least part of the first information and the second information.

In some embodiments, the processing device 120 may determine the target image based on a difference between the image and the at least part of the first information and the second information. For example, the processing device 120 may determine the target image by removing the first information (e.g., the first image associated with the first type of artifact) and the second information (e.g., the second image associated with the second type of artifact) from the image. Specifically, the processing device 120 may determine the target image by subtracting a first pixel value (e.g., a gray value, a Hounsfield unit (HU) value) of each first pixel of a plurality of first pixels in the first image associated with the first type of artifact and a second pixel value (e.g., a gray value, a Hounsfield unit (HU) value) of each corresponding second pixel of a plurality of second pixels in the second image associated with the second type of artifact from a third pixel value (e.g., a gray value, a Hounsfield unit (HU) value) of a corresponding third pixel in the image.

For illustration purposes, an artifact correction process of a CT image is taken as an example, the processing device 120 may obtain a CT image. The CT image may include a cupping artifact and a streak artifact. The processing device 120 may determine first information associated with the cupping artifact (e.g., a first image associated with the cupping artifact) and second information associated with the streak artifact (e.g., a second image associated with the streak artifact) by inputting the CT image into a trained machine learning model (e.g., a trained UNet and a trained ResNet). Specifically, the trained UNet may output the first information associated with the cupping artifact (e.g., the first image associated with the cupping artifact) by processing the CT image. The trained ResNet may output the second information associated with the streak artifact (e.g., the second image associated with the streak artifact) by processing the output of the trained UNet. The processing device 120 may generate the target image (i.e., a corrected CT image) by removing the first information and the second information from the CT image. Specifically, the processing device 120 may determine the target image by subtracting a first pixel value (e.g., a gray value, a Hounsfield unit (HU) value) of each first pixel of a plurality of first pixels in the first image associated with the cupping artifact and a second pixel value (e.g., a gray value, a Hounsfield unit (HU) value) of each corresponding second pixel of a plurality of second pixels in the second image associated with the streak artifact from a third pixel value (e.g., a gray value, a Hounsfield unit (HU) value) of a corresponding third pixel in the CT image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the trained machine learning model may further include a third trained model. The third trained model may be configured to determine third information associated with a third type of artifact in the image. The third trained model and the second trained model may be cascaded. That is, an output of the second trained model may be an input of the third trained model.

Figure 6:
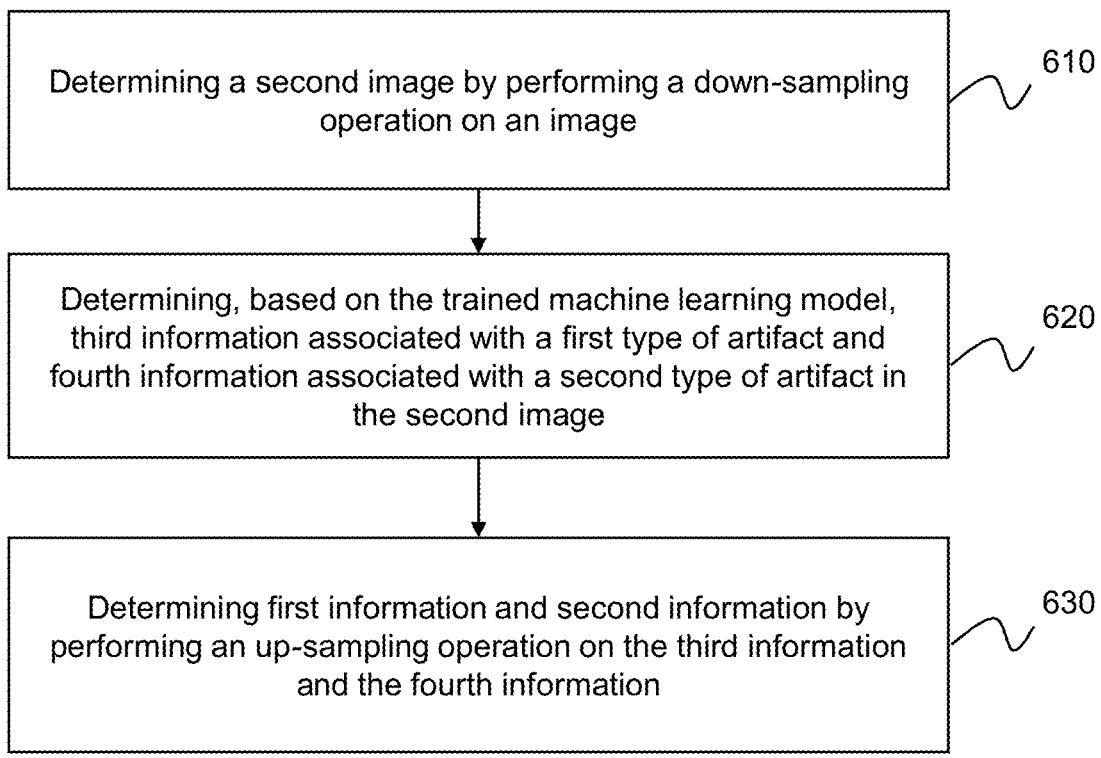
FIG. 6 is a flowchart illustrating an exemplary process for determining first information and second information according to some embodiments of the present disclosure.

FIG. 6 is a flowchart illustrating an exemplary process for determining first information and second information according to some embodiments of the present disclosure. In some embodiments, the process 600 may be implemented in the image processing system 100 illustrated in FIG. 1. For example, the process 600 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 120 (e.g., the determination module 420) may determine a second image by performing a down-sampling operation on an image.

As used herein, a down-sampling may refer to a process for reducing a sampling rate of a signal, e.g., reducing a size of an image. A down-sampling operation may be typically used to reduce a storage and/or a bandwidth needs for transmission of an image. In some embodiments, the down-sampling operation may be performed according to a down-sampling factor (e.g., K). For example, the processing device 120 may perform the down-sampling operation on the image by setting a pixel value of a pixel in an output image (i.e., the second image) to an average value of one or more pixel values of one or more pixels in a corresponding K×K blocks in an input image (i.e., the image).

In some embodiments, the down-sampling factor may be an integer or a rational fraction greater than 1. For example, the down-sampling factor may be 2, 3, 4, 5, or the like. In some embodiments, the down-sampling factor may be a default parameter stored in a storage device (e.g., the storage device 130). Additionally or alternatively, the down-sampling factor may be set manually or determined by one or more components of the image processing system 100 according to different situations. For example, the down-sampling factor may be determined based on a processing power of the processing device 120.

In 620, the processing device 120 (e.g., the determination module 420) may determine, based on the trained machine learning model, third information associated with a first type of artifact and fourth information associated with a second type of artifact in the second image.

In some embodiments, the first type of artifact may be a low frequency artifact, and the second type of artifact may be a high frequency artifact as described elsewhere in the present disclosure. In some embodiments, the third information may be an image associated with the first type of artifact, and the fourth information may be an image associated with the second type of artifact. In some embodiments, the processing device 120 may determine the third information and the fourth information based on the second image according to the trained machine learning model as described in connection with operation 520.

In 630, the processing device 120 (e.g., the determination module 420) may determine first information and second information by performing an up-sampling operation on the third information and the fourth information.

As used herein, an up-sampling may refer to a process for increasing a sampling rate of a signal, e.g., increasing a size of an image. An up-sampling operation may be typically used to increase a resolution of an image. In some embodiments, the up-sampling operation may be performed according to an up-sampling factor. In some embodiments, the up-sampling factor may be the same as the down-sampling factor. Accordingly, a resolution of an image associated with the first type of artifact (i.e., the first information) and a resolution of an image associated with the second type of artifact (i.e., the second information) may be the same as a resolution of the image. In some embodiments, the up-sampling factor may be different from the down-sampling factor. In some embodiments, the up-sampling factor may be a default parameter stored in a storage device (e.g., the storage device 130). Additionally or alternatively, the up-sampling factor may be set manually or determined by one or more components of the image processing system 100 according to different situations.

In some embodiments, the processing device 120 may perform the up-sampling operation on the third information and the fourth information based on an up-sampling algorithm. Exemplary up-sampling algorithms may include a linear interpolation algorithm, a nearest-neighbor interpolation algorithm, a bilinear interpolation algorithm, a mean interpolation algorithm, a median interpolation algorithm, a sinc-interpolation algorithm, a cubic convolution algorithm, or the like.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
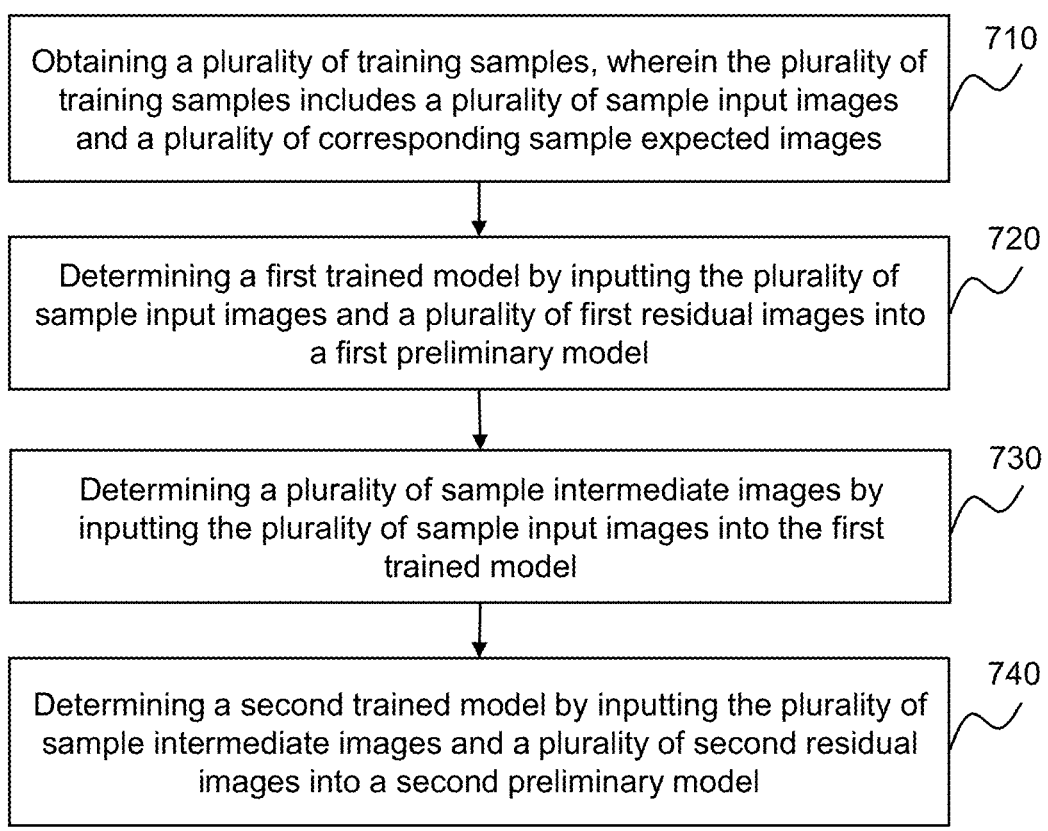
FIG. 7 is a flowchart illustrating an exemplary process for determining a trained machine learning model according to some embodiments of the present disclosure.

FIG. 7 is a flowchart illustrating an exemplary process for determining a trained machine learning model according to some embodiments of the present disclosure. In some embodiments, the process 700 may be implemented in the image processing system 100 illustrated in FIG. 1. For example, the process 700 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 120 (e.g., the obtaining module 410) may obtain a plurality of training samples. The plurality of training samples may include a plurality of sample input images and a plurality of corresponding sample expected images. Each of the plurality of corresponding sample expected images may be determined by performing an artifact correction operation on a sample input image.

In some embodiments, the sample input image may include a first type of artifact and/or a second type of artifact. In some embodiments, the first type of artifact may be a low frequency artifact, and the second type of artifact may be a high frequency artifact. For example, the first type of artifact may be a cupping artifact and the second type of artifact may be a streak artifact. In some embodiments, the first type of artifact and/or the second type of artifact may be a bone induced artifact. For example, the first type of artifact and/or the second type of artifact may be a bone hardening artifact.

In some embodiments, the processing device 120 may obtain a plurality of historical images from one or more components (e.g., the imaging device 110, the terminal 140, and/or the storage device 130) of the image processing system 100 or an external storage device via the network 150. The plurality of historical images may be associated with a plurality of historical imaging processes and/or historical treatment processes in a historical time period (e.g., last one week, last one month, last one year). The processing device 120 may determine the plurality of historical images as the sample input images. The processing device 120 may determine the plurality of corresponding sample expected images by performing the artifact correction operation on the plurality of sample input images. In some embodiments, the processing device 120 may perform the artifact correction operation on the plurality of sample input images according to an artifact correction algorithm. Exemplary artifact correction algorithms may include an empirical beam hardening correction (EBHC), a segmentation-free empirical beam hardening correction (Sf-EBHC), a polar coordinate conversion based correction, or the like.

In some embodiments, the processing device 120 may obtain historical projection data from one or more components (e.g., the imaging device 110, the terminal 140, and/or the storage device 130) of the image processing system 100 or an external storage device via the network 150. The projection data may be generated by the imaging device 110 via imaging a subject or a part of the subject. The processing device 120 may determine the sample input image based on the projection data according to a reconstruction algorithm without artifact correction. Exemplary reconstruction algorithms without artifact correction may include a filtered back projection reconstruction algorithm, or the like. The processing device 120 may determine the corresponding sample expected image based on the projection data according to a reconstruction algorithm including artifact correction. Exemplary reconstruction algorithms including artifact correction may include a polynomial-based artifact correction algorithm, an iterative beam hardening correction algorithm (IBHC), or the like.

In 720, the processing device 120 (e.g., the training module 440) may determine a first trained model by inputting the plurality of sample input images and a plurality of first residual images into a first preliminary model.

In some embodiments, each of the plurality of first residual images may relate to a difference between a sample input image and a corresponding sample expected image. In some embodiments, the processing device 120 may determine the difference between the sample input image and the corresponding sample expected image by performing a subtraction operation between the sample input image and the corresponding sample expected image. For example, the processing device 120 may determine the first residual image by subtracting a pixel value of each pixel of a plurality of pixels in the sample input image from a pixel value of each corresponding pixel in the corresponding sample expected image.

The first preliminary model may refer to a machine learning model to be trained. In some embodiments, the first preliminary model may be suitable for training to determine first information associated with a first type of artifact (e.g., a low frequency artifact) in an image. For example, the first preliminary model may be a preliminary UNet. The first preliminary model may include one or more model parameters. In some embodiments, the model parameter(s) may have one or more initial values. In some embodiments, the initial values of the model parameter(s) may be default values determined by the image processing system 100 or preset by a user of the image processing system 100. In some embodiments, the processing device 120 may obtain the first preliminary model from a storage device (e.g., the storage device 130) of the image processing system 100 and/or an external storage device via the network 150.

In some embodiments, the processing device 120 may input the plurality of sample input images and the plurality of first residual images into the first preliminary model and train the first preliminary model. In some embodiments, the processing device 120 may perform one or more training processes until all the sample input images and the corresponding first residual images are used for training. In some embodiments, the processing device 120 may generate an updated model in each round of the training process. For example, the processing device 120 may input one or more of the plurality of sample input images and corresponding first residual images into the first preliminary model in one round of a first training process to generate a first updated model, and then the processing device 120 may input one or more other sample input images and corresponding first residual images into the first updated model in the same round of a second training process to generate a second updated model. In some embodiments, one or more iterations of the training process may be performed until all the sample input images and the corresponding first residual images are used for training, and a first trained model may be obtained.

In a training process, the processing device 120 may process one or more of the plurality of sample input images and corresponding first residual images in an initial layer of a machine learning model (e.g., the first preliminary or updated model), and the processing result may serve as input data for a next layer of the first preliminary or updated model. The processing device 120 may process input data of each layer of the first preliminary or updated model obtained from a preceding layer. The processing device 120 may generate an output from a last layer of the first preliminary or updated model. The output generated from the last layer may include one or more updated model parameters relating to the machine learning model, one or more intermediate images (e.g., first information) generated after one or more input images pass through all layers of the machine learning model, or the like. In some embodiments, the processing device 120 may compare an intermediate image to a first residual image corresponding to an input image that generates the intermediate image. In some embodiments, the processing device 120 may update the model parameters of the first preliminary or updated model based on the result of the comparison to obtain a newly updated model, so that the newly updated model may be used to generate an intermediate image that is closer to the first residual image than a previous model (e.g., the first preliminary or updated model).

In some embodiments, the processing device 120 may determine whether a condition is satisfied. The condition may relate to an iteration count representing the number of iterations that have been performed, a degree of change in one or more model parameters updated in a current iteration comparing with those updated in a previous iteration, a difference between an output image (e.g., first information) generated using the currently updated model and a corresponding first residual image, or the like, or any combination thereof.

In response to a determination that the condition is satisfied (e.g., the iteration count reaches a first threshold, the degree of change in one or more model parameters between successive iterations is below a second threshold, or the difference between the output image (e.g., the first information) generated using the currently updated model and the corresponding first residual image is less than a third threshold), the processing device 120 may determine that the corresponding updated model obtained at the last iterative operation is sufficiently trained. The processing device 120 may designate the updated model as the first trained model. The first trained model may be configured to determine first information associated with a first type of artifact in an image, as described elsewhere in the present disclosure (e.g., FIG. 5, and descriptions thereof).

In response to a determination that the condition is not satisfied (e.g., the iteration count is less than the first threshold, the degree of change in one or more model parameters between successive iterations is more than the second threshold, the difference between the output image (e.g., the first information) generated using the currently updated model and the corresponding expected image exceeds the third threshold), the processing device 120 may perform one or more iterations for further updating the updated model until the condition is satisfied.

It should be noted that, in response to a determination that the iteration count is equal to the first threshold, the degree of change in one or more model parameters between successive iterations is equal to the second threshold, or the difference between the output image (e.g., the first information) generated using the currently updated model and the corresponding expected image is equal to the third threshold, the processing device 120 may either determine that the condition is satisfied or determine that the condition is not satisfied.

In 730, the processing device 120 (e.g., the training module 440) may determine a plurality of sample intermediate images by inputting the plurality of sample input images into the first trained model.

For example, the processing device 120 may input the plurality of sample input images into the first trained model. The first trained model may generate the plurality of sample intermediate images. In some embodiments, the sample intermediate image may be associated with the first type of artifact in the corresponding sample input image.

In 740, the processing device 120 (e.g., the training module 440) may determine a second trained model by inputting the plurality of sample intermediate images and a plurality of second residual images into a second preliminary model.

In some embodiments, each of the plurality of second residual images may relate to a difference between a sample intermediate image and a corresponding first residual image. In some embodiments, the processing device 120 may determine the difference between a sample intermediate image and a corresponding first residual image by performing a subtraction operation between the sample intermediate image and the corresponding first residual image. For example, the processing device 120 may determine the second residual image by subtracting a pixel value of each pixel of a plurality of pixels in the sample intermediate image from a pixel value of each corresponding pixel in the corresponding first residual image.

In some embodiments, the second preliminary model may be the same as or different from the first preliminary model. In some embodiments, the second preliminary model may be suitable for training to determine second information associated with a second type of artifact (e.g., a high frequency artifact) in an image. For example, the second preliminary model may be a preliminary ResNet. The second trained model may be generated by training the second preliminary model as described in connection with the training of the first preliminary model. In some embodiments, the training process of the second trained model may be the same as or different from the training process of the first trained model.

For illustration purposes, a training process of a preliminary machine learning model (e.g., a first preliminary model and a second preliminary model) is taken as an example, the sample input image may be a CT image including a low frequency artifact (e.g., a cupping artifact) and a high frequency artifact (e.g., a streak artifact). The corresponding sample expected image may be a corrected CT image without the low frequency artifact (e.g., the cupping artifact) and the high frequency artifact (e.g., the streak artifact). The first residual image may be associated with the low frequency artifact (e.g., the cupping artifact) and the high frequency artifact (e.g., the streak artifact). The second residual image may be associated with the high frequency artifact (e.g., the streak artifact). The processing device 120 may determine a first trained model (e.g., a trained UNet) by inputting a plurality of sample input images and a plurality of first residual images into the first preliminary model (e.g., a preliminary UNet). The first preliminary model (e.g., the preliminary UNet) may be suitable for training to determine first information associated with the low frequency artifact (e.g., the cupping artifact) in the CT image. The processing device 120 may determine a plurality of sample intermediate images by inputting the plurality of sample input images into the first trained model (e.g., the trained UNet). The sample intermediate image of the first trained model may be associated with the low frequency artifact (e.g., the cupping artifact) in the CT image. The processing device 120 may determine a second trained model (e.g., a trained ResNet) by inputting the plurality of sample intermediate images and a plurality of second residual images into the second preliminary model (e.g., a preliminary ResNet). The second preliminary model (e.g., the preliminary ResNet) may be suitable for training to determine second information associated with the high frequency artifact (e.g., the streak artifact) in the CT image. An output image of the second trained model may be associated with the high frequency artifact (e.g., the streak artifact) in the CT image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more other optional operations (e.g., a storing operation) may be added elsewhere in the exemplary process 700. In the storing operation, the processing device 120 may store information and/or data associated with the first trained model and the second trained model (e.g., the plurality of input images, the plurality of expected images, the plurality of first residual images, the plurality of second residual images, the plurality of output images) in a storage device (e.g., the storage device 130) disclosed elsewhere in the present disclosure.

In some embodiments, the trained machine learning model may be updated from time to time, e.g., periodically or not, based on a plurality of training samples that is at least partially different from the plurality of original training samples from which the original trained machine learning model is determined. For instance, the trained machine learning model may be updated based on training samples including new training samples that are not in the original training samples, training samples processed using the machine learning model in connection with the original trained machine learning model of a prior version, or the like, or a combination thereof. In some embodiments, the determination and/or updating of the trained machine learning model may be performed on a processing device, while the application of the trained machine learning model may be performed on a different processing device. In some embodiments, the determination and/or updating of the trained machine learning model may be performed on a processing device of a system different than the image processing system 100 or a server different than a server including the processing device 120 on which the application of the trained machine learning model is performed. For instance, the determination and/or updating of the trained machine learning model may be performed on a first system of a vendor who provides and/or maintains such a machine learning model and/or has access to training samples used to determine and/or update the trained machine learning model, while image processing based on the provided machine learning model may be performed on a second system of a client of the vendor. In some embodiments, the determination and/or updating of the trained machine learning model may be performed online in response to a request for image processing. In some embodiments, the determination and/or updating of the trained machine learning model may be performed offline.

Figure 8:
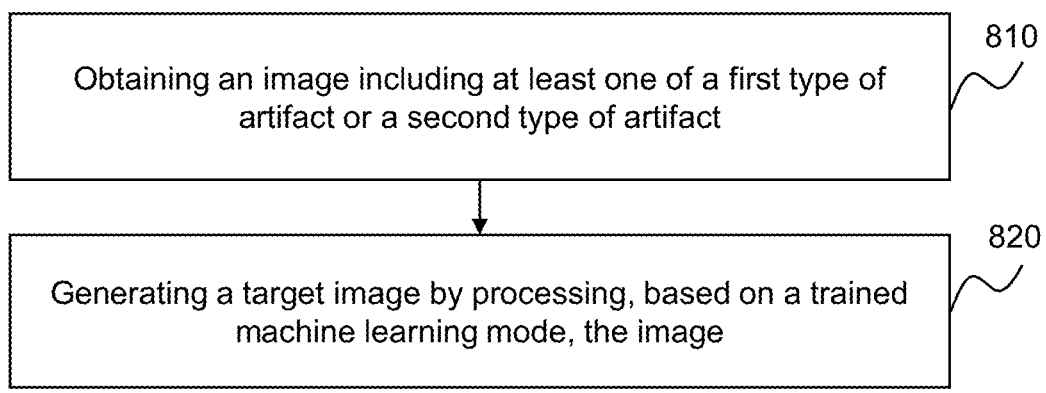
FIG. 8 is a flowchart illustrating an exemplary process for generating a target image according to some embodiments of the present disclosure.

FIG. 8 is a flowchart illustrating an exemplary process for generating a target image according to some embodiments of the present disclosure. In some embodiments, the process 800 may be implemented in the image processing system 100 illustrated in FIG. 1. For example, the process 800 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 120 (e.g., the obtaining module 410) may obtain an image including at least one of a first type of artifact or a second type of artifact. More descriptions of the obtaining of the image may be found elsewhere in the present disclosure (e.g., operation 510 in FIG. 5, and descriptions thereof).

In 820, the processing device 120 (e.g., the generation module 430) may generate a target image by processing, based on a trained machine learning model, the image.

In some embodiments, the processing device 120 may generate the target image based on the image according to the trained machine learning model. In some embodiments, the trained machine learning model may be a two-step convolutional neural network (CNN). For example, the trained machine learning model may include a first trained model and a second trained model. The first trained model and the second trained model may be cascaded. That is, an output of the first trained model may be an input of the second trained model. The first trained model may be configured to correct the first type of artifact in the image, and the second trained model may be configured to correct the second type of artifact in the image. In some embodiments, the first trained model and/or the second trained model may include a U-shape network (UNet), a residual network (ResNet), a dense convolutional network (DenseNet), a generative adversarial network (GAN), or the like, or any combination thereof. For example, the first trained model may be a UNet, and the second trained model may be a ResNet.

In some embodiments, the processing device 120 may input the image into the first trained model. The first trained model may correct the first type of artifact in the image and output a first corrected image. The processing device 120 may input the first corrected image into the second trained model. The second trained model may correct the second type of artifact in the first corrected image and output a second corrected image (e.g., the target image). For illustration purposes, an artifact correction process of a CT image is taken as an example, the processing device 120 may obtain a CT image. The CT image may include a cupping artifact and a streak artifact. The processing device 120 may determine a target image (i.e., a corrected CT image) by inputting the CT image into a trained machine learning model (e.g., a trained UNet and a trained ResNet). Specifically, the processing device 120 may input the CT image into the trained UNet. The trained UNet may output a cupping artifact corrected image by correcting the cupping artifact in the CT image. The processing device 120 may input the cupping artifact corrected image into the trained ResNet. The trained ResNet may output a streak artifact corrected image (i.e., the target image) by correcting the streak artifact in the cupping artifact corrected image.

The trained machine learning model may be determined by training a preliminary machine learning model. The preliminary machine learning model may include a first preliminary model and a second preliminary model. For example, the first trained model may be determined by training the first preliminary model, and the second trained model may be determined by training the second preliminary model. In some embodiments, the preliminary machine learning model (e.g., the first preliminary model, the second preliminary model) may include one or more algorithms used for generating an output result (e.g., the target image) based on input image data (e.g., the image). The trained machine learning model may include one or more relatively optimized parameters relating to the algorithms (e.g., the CNN) of the preliminary machine learning model, so that the sufficiency and/or accuracy of artifact removal based on the trained machine learning model may be satisfactory for practical use.

In some embodiments, the trained machine learning model may be generated by one or more other processors inside and/or outside the image processing system 100. In some embodiments, the processing device 120 may directly obtain the trained machine learning model, e.g., from the storage device 130. More descriptions of the determination of the trained machine learning model may be found elsewhere in the present disclosure (e.g., FIG. 9 and descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the trained machine learning model may further include a third trained model. The third trained model may be configured to correct a third type of artifact in the image. The third trained model and the second trained model may be cascaded. That is, an output of the second trained model may be an input of the third trained model.

Figure 9:
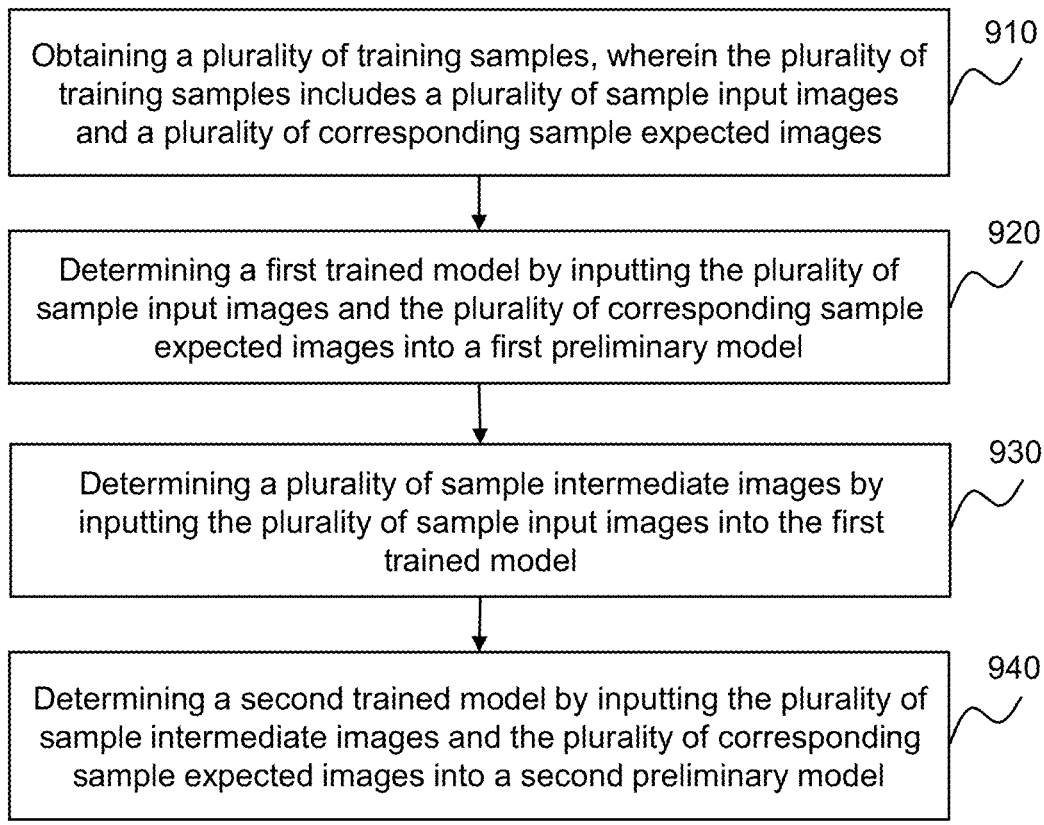
FIG. 9 is a flowchart illustrating an exemplary process for determining a trained machine learning model according to some embodiments of the present disclosure.

FIG. 9 is a flowchart illustrating an exemplary process for determining a trained machine learning model according to some embodiments of the present disclosure. In some embodiments, the process 900 may be implemented in the image processing system 100 illustrated in FIG. 1. For example, the process 900 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, the processing device 120 (e.g., the obtaining module 410) may obtain a plurality of training samples. The plurality of training samples may include a plurality of sample input images and a plurality of corresponding sample expected images.

More descriptions of the obtaining of the plurality of training samples may be found elsewhere in the present disclosure (e.g., operation 710 in FIG. 7, and descriptions thereof).

In 920, the processing device 120 (e.g., the training module 440) may determine a first trained model by inputting the plurality of sample input images and the plurality of corresponding sample expected images into a first preliminary model.

The first preliminary model may refer to a machine learning model to be trained. In some embodiments, the first preliminary model may be suitable for training to correct a first type of artifact (e.g., a low frequency artifact) in an image. For example, the first preliminary model may be a preliminary UNet. The first preliminary model may include one or more model parameters. In some embodiments, the model parameter(s) may have one or more initial values. In some embodiments, the initial values of the model parameter(s) may be default values determined by the image processing system 100 or preset by a user of the image processing system 100. In some embodiments, the processing device 120 may obtain the first preliminary model from a storage device (e.g., the storage device 130) of the image processing system 100 and/or an external storage device via the network 150.

In some embodiments, the processing device 120 may input the plurality of sample input images and the plurality of corresponding sample expected images into the first preliminary model and train the first preliminary model. In some embodiments, the processing device 120 may perform one or more training processes until all the sample input images and the corresponding sample expected images are used for training. In some embodiments, the processing device 120 may generate an updated model in each round of the training process. For example, the processing device 120 may input one or more of the plurality of sample input images and corresponding sample expected images into the first preliminary model in one round of a first training process to generate a first updated model, and then the processing device 120 may input one or more other sample input images and corresponding sample expected images into the first updated model in the same round of a second training process to generate a second updated model. In some embodiments, one or more iterations of the training process may be performed until all the sample input images and the corresponding sample expected images are used for training, and the first trained model may be obtained.

In a training process, the processing device 120 may process one or more of the plurality of sample input images and corresponding sample expected images in an initial layer of a machine learning model (e.g., the first preliminary or updated model), and the processing result may serve as input data for a next layer of the first preliminary or updated model. The processing device 120 may process input data of each layer of the first preliminary or updated model obtained from a preceding layer. The processing device 120 may generate an output from a last layer of the first preliminary or updated model. The output generated from the last layer may include one or more updated model parameters relating to the machine learning model, one or more intermediate images generated after one or more input images pass through all layers of the machine learning model, or the like. In some embodiments, the processing device 120 may compare an intermediate image to an expected image corresponding to an input image that generates the intermediate image. In some embodiments, the processing device 120 may update the model parameters of the first preliminary or updated model based on the result of the comparison to obtain a newly updated model, so that the newly updated model may be used to generate an intermediate that is closer to the expected image than a previous model (e.g., the first preliminary or updated model).

In some embodiments, the processing device 120 may determine whether a condition is satisfied. The condition may relate to an iteration count representing the number of iterations that have been performed, a degree of change in one or more model parameters updated in a current iteration comparing with those updated in a previous iteration, a difference between an output image generated using the currently updated model and a corresponding expected image, or the like, or any combination thereof.

In response to a determination that the condition is satisfied (e.g., the iteration count reaches a first threshold, the degree of change in one or more model parameters between successive iterations is below a second threshold, or the difference between the output image generated using the currently updated model and the corresponding expected image is less than a third threshold), the processing device 120 may determine that the corresponding updated model obtained at the last iterative operation is sufficiently trained. The processing device 120 may designate the updated model as the first trained model. The first trained model may be configured to correct the first type of artifact in the image, as described elsewhere in the present disclosure (e.g., FIG. 8, and descriptions thereof).

In response to a determination that the condition is not satisfied (e.g., the iteration count is less than the first threshold, the degree of change in one or more model parameters between successive iterations is more than the second threshold, the difference between the output image generated using the currently updated model and the corresponding expected image exceeds the third threshold), the processing device 120 may perform one or more iterations for further updating the updated model until the condition is satisfied.

It should be noted that, in response to a determination that the iteration count is equal to the first threshold, the degree of change in one or more model parameters between successive iterations is equal to the second threshold, or the difference between the output image (e.g., the first information) generated using the currently updated model and the corresponding expected image is equal to the third threshold, the processing device 120 may either determine that the condition is satisfied or determine that the condition is not satisfied.

In 930, the processing device 120 (e.g., the training module 440) may determine a plurality of sample intermediate images by inputting the plurality of sample input images into the first trained model.

For example, the processing device 120 may input the plurality of sample input images into the first trained model. The first trained model may correct the first type of artifact in the plurality of sample input images and generate the plurality of sample intermediate images. In some embodiments, the sample intermediate image may be a first type of artifact corrected image.

In 940, the processing device 120 (e.g., the training module 440) may determine a second trained model by inputting the plurality of sample intermediate images and the plurality of corresponding sample expected images into a second preliminary model.

In some embodiments, the second preliminary model may be the same as or different from the first preliminary model. In some embodiments, the second preliminary model may be suitable for training to correct a second type of artifact (e.g., a high frequency artifact) in an image. For example, the second preliminary model may be a preliminary ResNet. The second trained model may be generated by training the second preliminary model as described in connection with the training of the first preliminary model. In some embodiments, the training process of the second trained model may be the same as or different from the training process of the first trained model.

For illustration purposes, a training process of a preliminary machine learning model (e.g., a first preliminary model and a second preliminary model) is taken as an example, the sample input image may be a CT image including a low frequency artifact (e.g., a cupping artifact) and a high frequency artifact (e.g., a streak artifact). The sample expected image may be a corrected CT image without the low frequency artifact (e.g., the cupping artifact) and the high frequency artifact (e.g., the streak artifact). The processing device 120 may determine a first trained model (e.g., a trained UNet) by inputting a plurality of sample input images and a plurality of sample expected images into a first preliminary model (e.g., a preliminary UNet). The first preliminary model (e.g., the preliminary UNet) may be suitable for training to correct the low frequency artifact (e.g., the cupping artifact) in the CT image. The processing device 120 may determine a plurality of sample intermediate images by inputting the plurality of sample input images into the first trained model (e.g., the trained UNet). The sample intermediate image of the first trained model may be a low frequency artifact corrected CT image. The processing device 120 may determine a second trained model (e.g., a trained ResNet) by inputting the plurality of sample intermediate images and the plurality of sample expected images into a second preliminary model (e.g., a preliminary ResNet). The second preliminary model (e.g., the preliminary ResNet) may be suitable for training to correct the high frequency artifact (e.g., the streak artifact) in the CT image. An output image of the second trained model may be a corrected CT image without the low frequency artifact (e.g., the cupping artifact) and the high frequency artifact (e.g., the streak artifact).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more other optional operations (e.g., a storing operation) may be added elsewhere in the exemplary process 900. In the storing operation, the processing device 120 may store information and/or data associated with the first trained model and the second trained model (e.g., the plurality of input images, the plurality of expected images, the plurality of output images) in a storage device (e.g., the storage device 130) disclosed elsewhere in the present disclosure.

In some embodiments, the trained machine learning model may be updated from time to time, e.g., periodically or not, based on a plurality of training samples that is at least partially different from the plurality of original training samples from which the original trained machine learning model is determined. For instance, the trained machine learning model may be updated based on training samples including new training samples that are not in the original training samples, training samples processed using the machine learning model in connection with the original trained machine learning model of a prior version, or the like, or a combination thereof. In some embodiments, the determination and/or updating of the trained machine learning model may be performed on a processing device, while the application of the trained machine learning model may be performed on a different processing device. In some embodiments, the determination and/or updating of the trained machine learning model may be performed on a processing device of a system different than the image processing system 100 or a server different than a server including the processing device 120 on which the application of the trained machine learning model is performed. For instance, the determination and/or updating of the trained machine learning model may be performed on a first system of a vendor who provides and/or maintains such a machine learning model and/or has access to training samples used to determine and/or update the trained machine learning model, while image processing based on the provided machine learning model may be performed on a second system of a client of the vendor. In some embodiments, the determination and/or updating of the trained machine learning model may be performed online in response to a request for image processing. In some embodiments, the determination and/or updating of the trained machine learning model may be performed offline.

Figure 10:
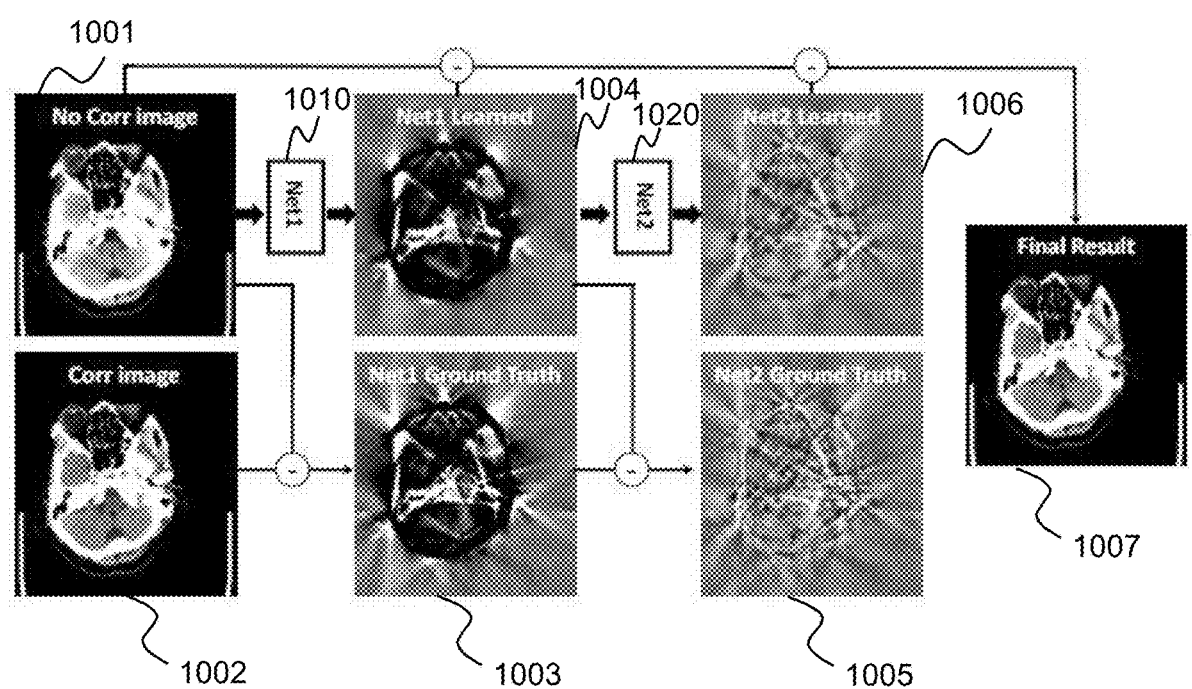
FIG. 10 is a schematic diagram illustrating an exemplary process for determining a trained machine learning model according to some embodiments of the present disclosure.

FIG. 10 is a schematic diagram illustrating an exemplary process for determining a trained machine learning model according to some embodiments of the present disclosure. As illustrated in FIG. 10, the processing device 120 may obtain a plurality of training samples. The plurality of training samples may include a plurality of sample input images 1001 and a plurality of corresponding sample expected images 1002. Each of the plurality of sample input images 1001 may be an original CT image including a low frequency artifact and a high frequency artifact. Each of the plurality of corresponding sample expected images 1002 may be determined by performing an artifact correction operation on the sample input image 1001. The processing device 120 may determine a plurality of first residual images 1003 by performing a subtraction operation between the each of the plurality of sample input images 1001 and the corresponding sample expected image 1002. The processing device 120 may determine a first trained model 1010 by inputting the plurality of sample input images 1001 and the plurality of first residual images 1003 into a first preliminary model. The processing device 120 may determine a plurality of sample intermediate images 1004 by inputting the plurality of sample input images 1001 into the first trained model 1010. The sample intermediate image 1004 may be associated with the low frequency artifact in the original CT image (i.e., the input image 1001). The processing device 120 may determine a plurality of second residual images 1005 by performing a subtraction operation between each of the plurality of sample intermediate images 1004 and the corresponding first residual image 1003. The processing device 120 may determine a second trained model 1020 by inputting the plurality of sample intermediate images 1004 and the plurality of second residual images 1005 into a second preliminary model. The output image 1006 may be associated with the high frequency artifact in the original CT image (i.e., the input image 1001). The processing device 120 may generate a target image 1007 (e.g., a corrected CT image) based on the original CT image, the sample intermediate image 1004, and the output image 1006. For example, the processing device 120 may determine the target image 1007 by performing a subtraction operation on the original CT image, the sample intermediate image 1004, and the output image 1006.

Figure 11:
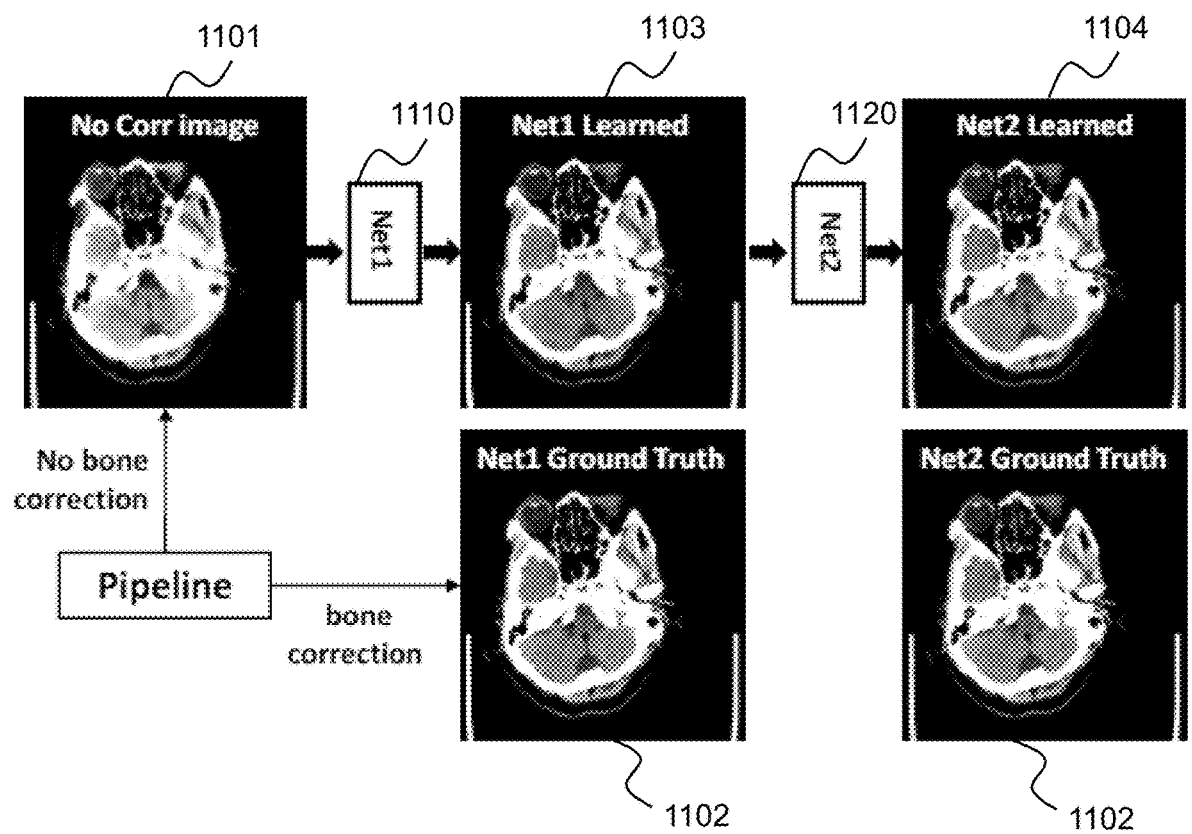
FIG. 11 is a schematic diagram illustrating an exemplary process for determining a trained machine learning model according to some embodiments of the present disclosure.

FIG. 11 is a schematic diagram illustrating an exemplary process for determining a trained machine learning model according to some embodiments of the present disclosure. As illustrated in FIG. 11, the processing device 120 may obtain a plurality of training samples. The plurality of training samples may include a plurality of sample input images 1101 and a plurality of corresponding sample expected images 1102. Each of the plurality of sample input images 1101 may be an original CT image including a low frequency artifact and a high frequency artifact. Each of the plurality of corresponding sample expected images 1102 may be determined by performing an artifact correction operation (e.g., a bone correction operation) on the sample input image 1101. The processing device 120 may determine a first trained model 1110 by inputting the plurality of sample input images 1101 and the plurality of corresponding sample expected images 1102 into a first preliminary model. The processing device 120 may determine a plurality of sample intermediate images 1103 by inputting the plurality of sample input images 1101 into the first trained model 1010. The sample intermediate image 1103 may be a low frequency artifact corrected CT image. The processing device 120 may determine a second trained model 1120 by inputting the plurality of sample intermediate images 1103 and the plurality of corresponding sample expected images 1102 into a second preliminary model. The output image 1004 (i.e., a target image) may be a low frequency artifact and high frequency artifact corrected CT image.

Figure 12:
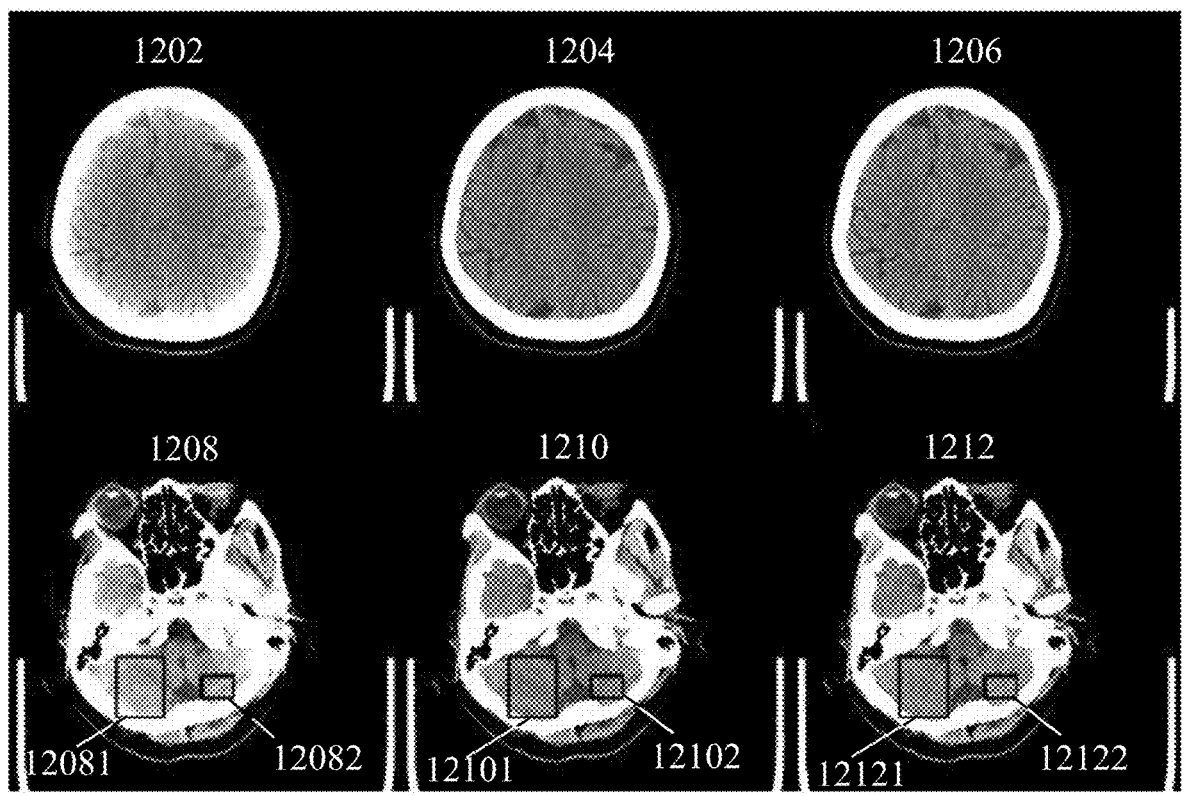
FIG. 12 is schematic diagram illustrating exemplary CT images corrected by a first trained model according to some embodiments of the present disclosure.

FIG. 12 is schematic diagram illustrating exemplary CT images corrected by a first trained model according to some embodiments of the present disclosure.

As illustrated in FIG. 12, 1202 refers to an original calvarium CT image without bone hardening correction, and 1208 refers to an original cranial base CT image without bone hardening correction. The reference numeral 1204 refers to a first corrected calvarium CT image, and 1210 refers to a first corrected cranial base CT image. The first corrected calvarium CT image 1204 and the first corrected cranial base CT image 1210 were determined by inputting the original calvarium CT image 1202 and the original cranial base CT image 1208 into a first trained model (e.g., a trained UNet), respectively. The reference numeral 1206 refers to a target calvarium CT image with bone hardening correction, and 1212 refers to a target cranial base CT image with bone hardening correction.

The original calvarium CT image 1202 includes a plurality of cupping artifacts, and the original cranial base CT image 1208 includes a plurality of cupping artifacts and a plurality of streak artifacts (shown in region 12081 and region 12082). The plurality of cupping artifacts in the first corrected calvarium CT image 1204 and the first corrected cranial base CT image 1210 were corrected by the trained UNet. That is, the trained UNet shows a good performance in correcting low frequency artifacts in the CT image, especially the cupping artifacts around the whole head skull. However, as shown in regions 12101 and 12102 in the first corrected cranial base CT image 1210, compared with corresponding regions 12121 and 12122 in the target cranial base CT image, the streak artifacts around fine skull structures remains in the first corrected cranial base CT image 1210. Furthermore, a noise pattern in the first corrected calvarium CT image 1204 (or the first corrected cranial base CT image 1210) is similar to a noise pattern in the target calvarium CT image 1206 (or the target cranial base CT image 1212).

Figure 13:
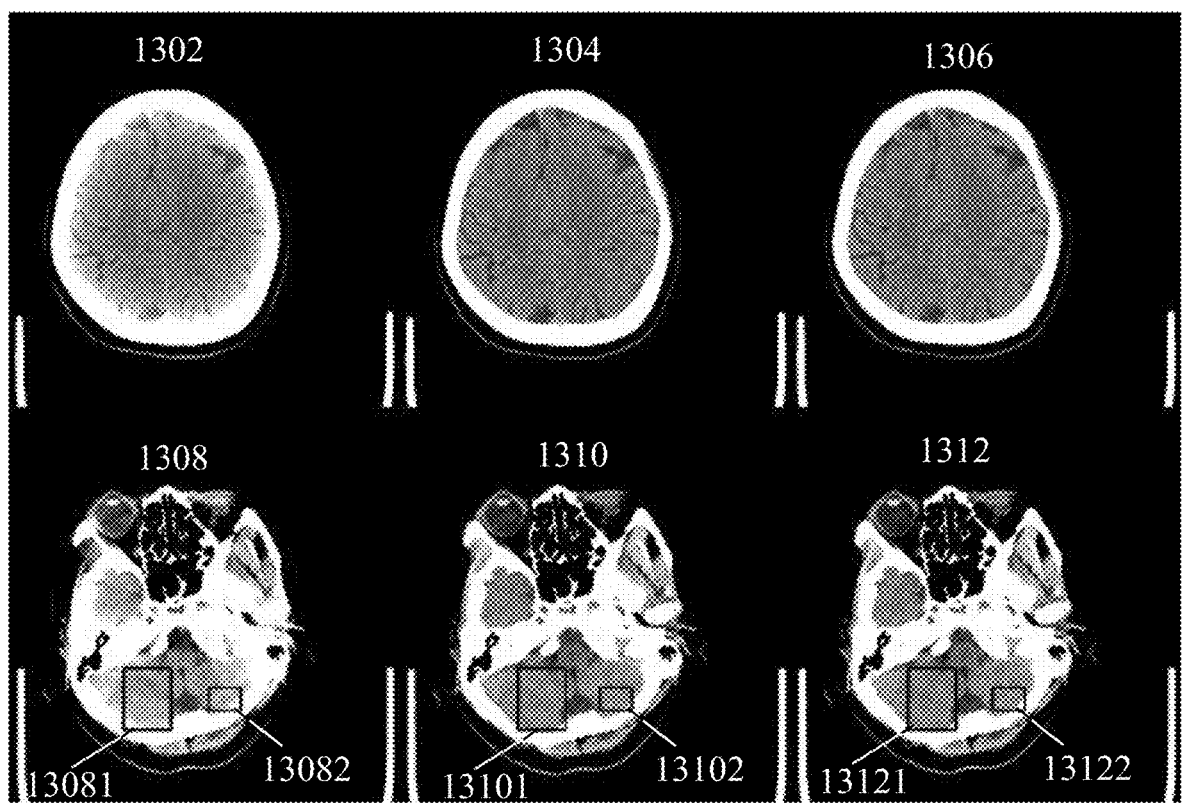
FIG. 13 is schematic diagram illustrating exemplary CT images corrected by a second trained model according to some embodiments of the present disclosure.

FIG. 13 is schematic diagram illustrating exemplary CT images corrected by a second trained model according to some embodiments of the present disclosure.

As illustrated in FIG. 13, 1302 refers to an original calvarium CT image without bone hardening correction, and 1308 refers to an original cranial base CT image without bone hardening correction. The reference numeral 1302 may be the same as or similar to 1202, and 1308 may be the same as or similar to 1208. The reference numeral 1304 refers to a second corrected calvarium CT image, and 1310 refers to a second corrected cranial base CT image. The second corrected calvarium CT image 1304 and the second corrected cranial base CT image 1310 were determined by inputting the first corrected calvarium CT image 1204 and the first corrected cranial base CT image 1210 into a second trained model (e.g., a trained ResNet). The reference numeral 1306 refers to a target calvarium CT image with bone hardening correction, and 1312 refers to a target cranial base CT image with bone hardening correction. The reference numeral 1306 may be the same as or similar to 1206, and 1312 may be the same as or similar to 1212.

The original calvarium CT image 1302 includes a plurality of cupping artifacts, and the original cranial base CT image 1308 includes a plurality of cupping artifacts and a plurality of streak artifacts (shown in region 13081 and region 13082). As shown in regions 13101 and 13102 in the second corrected cranial base CT image 1310, compared with corresponding regions 13121 and 13122 in the target cranial base CT image, the streak artifacts in the second corrected cranial base CT image 1310 were corrected by the trained ResNet. Furthermore, compared with the first corrected calvarium CT image 1204 including cupping artifacts, the second corrected calvarium CT image 1304 remains unchanged, without adding any artifacts. Accordingly, the trained ResNet shows a good performance in correcting high frequency artifacts in the CT image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A system comprising:
   at least one storage device storing a set of instructions; and
   at least one processor in communication with the at least one storage device, when executing the stored set of instructions, the at least one processor causes the system to perform operations including:
   obtaining an image including at least one of a first type of artifact or a second type of artifact;
   determining, based on a trained machine learning model, at least one of first information associated with the first type of artifact or second information associated with the second type of artifact in the image, wherein the trained machine learning model includes a first trained model and a second trained model, the first trained model being configured to determine the first information, the second trained model being configured to determine the second information, and the first trained model is obtained according to a process including:
      obtaining a plurality of training samples, wherein the plurality of training samples include a plurality of sample input images and a plurality of corresponding sample expected images, and each of the plurality of corresponding sample expected images is determined by performing an artifact correction operation on a sample input image; and
      determining the first trained model by inputting the plurality of sample input images and a plurality of first residual images into a first preliminary model, wherein each of the plurality of first residual images is determined by performing a subtraction operation between a sample input image and a corresponding sample expected image; and
   generating a target image based on at least part of the first information and the second information.

2. The system of claim 1, wherein the first trained model or the second trained model includes at least one of a U-shape network (UNet), a residual network (ResNet), a dense convolutional network (DenseNet), or a generative adversarial network (GAN).

3. The system of claim 1, wherein the second trained model is obtained according to a process including:

determining a plurality of sample intermediate images by inputting the plurality of sample input images into the first trained model; and determining the second trained model by inputting the plurality of sample intermediate images and a plurality of second residual images into a second preliminary model, wherein each of the plurality of second residual images relates to a difference between a sample intermediate image and a corresponding first residual image.

4. The system of claim 3, wherein the at least one processor causes the system to perform operations including:

determining the difference between a sample intermediate image and a corresponding first residual image by performing a subtraction operation between the sample intermediate image and the corresponding first residual image.

5. The system of claim 1, wherein to determine, based on a trained machine learning model, at least one of first information associated with the first type of artifact or second information associated with the second type of artifact in the image, the at least one processor causes the system to perform the operations including:

determining a second image by performing a down-sampling operation on the image;

determining, based on the trained machine learning model, at least one of third information associated with the first type of artifact or fourth information associated with the second type of artifact in the second image; and determining the at least one of the first information or the second information by performing an up-sampling operation on the at least one of the third information or the fourth information.

6. The system of claim 5, wherein the up-sampling operation includes a linear interpolation operation.

7. The system of claim 1, wherein the first type of artifact includes a low frequency artifact, and the second type of artifact includes a high frequency artifact.

8. The system of claim 7, wherein at least one of the first type of artifact or the second type of artifact is a bone induced artifact.

9. The system of claim 1, wherein the trained machine learning model is a convolutional neural network (CNN).

10. The system of claim 1, wherein the image includes at least one of a computed tomography (CT) image, a magnetic resonance imaging (MRI) image, a positron emission tomography (PET) image, an ultrasound image, or an X-ray image.

11. A system comprising:

at least one storage device storing a set of instructions; and at least one processor in communication with the at least one storage device, when executing the stored set of instructions, the at least one processor causes the system to perform operations including:

obtaining an image including at least one of a first type of artifact or a second type of artifact; and generating a target image by processing, based on a trained machine learning mode, the image, wherein the trained machine learning mode includes a first trained model and a second trained model, the first trained model being configured to correct the first type of artifact in the image, the second trained model being configured to correct the second type of artifact in the image, and the first trained model is obtained according to a process including:

obtaining a plurality of training samples, wherein the plurality of training samples include a plurality of sample input images and a plurality of corresponding sample expected images, and each of the plurality of corresponding sample expected images is determined by performing an artifact correction operation on a sample input image; and determining the first trained model by inputting the plurality of sample input images and a plurality of first residual images into a first preliminary model, wherein each of the plurality of first residual images is determined by performing a subtraction operation between a sample input image and a corresponding sample expected image.

12. The system of claim 11, wherein the second trained model is obtained according to a process including:

determining a plurality of sample intermediate images by inputting the plurality of sample input images into the first trained model; and determining the second trained model by inputting the plurality of sample intermediate images and the plurality of corresponding sample expected images into a second preliminary model.

13. The system of claim 11, wherein the first type of artifact includes a low frequency artifact, and the second type of artifact includes a high frequency artifact.

14. The system of claim 13, wherein at least one of the first type of artifact or the second type of artifact is a bone induced artifact.

15. A method for image processing implemented on a computing device having one or more processors and one or more storage devices, the method comprising:

obtaining an image including at least one of a first type of artifact or a second type of artifact;

determining, based on a trained machine learning model, at least one of first information associated with the first type of artifact or second information associated with the second type of artifact in the image, wherein the trained machine learning model includes a first trained model and a second trained model, the first trained model being configured to determine the first information, and the second trained model being configured to determine the second information, and the first trained model is obtained according to a process including:

obtaining a plurality of training samples, wherein the plurality of training samples include a plurality of sample input images and a plurality of corresponding sample expected images, and each of the plurality of corresponding sample expected images is determined by performing an artifact correction operation on a sample input image; and determining the first trained model by inputting the plurality of sample input images and a plurality of first residual images into a first preliminary model, wherein each of the plurality of first residual images is determined by performing a subtraction operation between a sample input image and a corresponding sample expected image; and generating a target image based on at least part of the first information and the second information.

* * * * *